United States Patent [19]

Hellstrom et al.

[11] 4,211,927
[45] Jul. 8, 1980

[54] COMPUTERIZED TOMOGRAPHY SYSTEM

[75] Inventors: Melbourne J. Hellstrom, Severna Park; Allen I. Perlin; Edward Kutlik, both of Baltimore, all of Md.

[73] Assignee: CGR Medical Corporation, Baltimore, Md.

[21] Appl. No.: 963,178

[22] Filed: Nov. 24, 1978

[51] Int. Cl.² ............................................. G03B 41/16
[52] U.S. Cl. ................................. 250/445 T; 250/491
[58] Field of Search ..................... 250/445 T, 490, 491

[56] References Cited

U.S. PATENT DOCUMENTS

| | | | |
|---|---|---|---|
| 3,809,886 | 5/1974 | Cochran et al. | 250/445 T |
| 4,087,694 | 5/1978 | Hellstrom et al. | 250/445 T |
| 4,095,110 | 6/1978 | Bunch | 250/445 T |
| 4,139,776 | 2/1979 | Hellstrom | 250/445 T |

Primary Examiner—Alfred E. Smith
Assistant Examiner—T. N. Grigsby
Attorney, Agent, or Firm—Brady, O'Boyle & Gates

[57] ABSTRACT

A tomographic system wherein a movable overhead support containing a tiltable X-ray source is non-mechanically coupled to an X-ray receptor beneath an examination table for effecting a desired type of tomographic sweep or scan under the direct control of a stored program microcomputer. Depending upon the parameters inputted to the computer by the operator, the computer enables self-centering control circuits for the source and receptor whereby they are independently brought into vertical alignment over the examination table and thereafter caused to move in opposite directions under precise control of synchronized and mathematically related pulse trains applied to respective stepper motors, first to a calculated reference position and then in predetermined mutual relationship to obtain a tomogram.

26 Claims, 19 Drawing Figures

| SWITCH LOGIC | |
|---|---|
| OVER TABLE TOP | = S1 + S4 |
| RIGHT OF CENTER | = S1 |
| CENTER | = $(\overline{S1}) \cdot (\overline{S2})$ |
| FAST | = $\overline{S3}$ |

CONTROL PROGRAM OVERVIEW

"MAIN" ROUTINE

"CENTER" SUBROUTINE

"START TOMO" SUBROUTINE

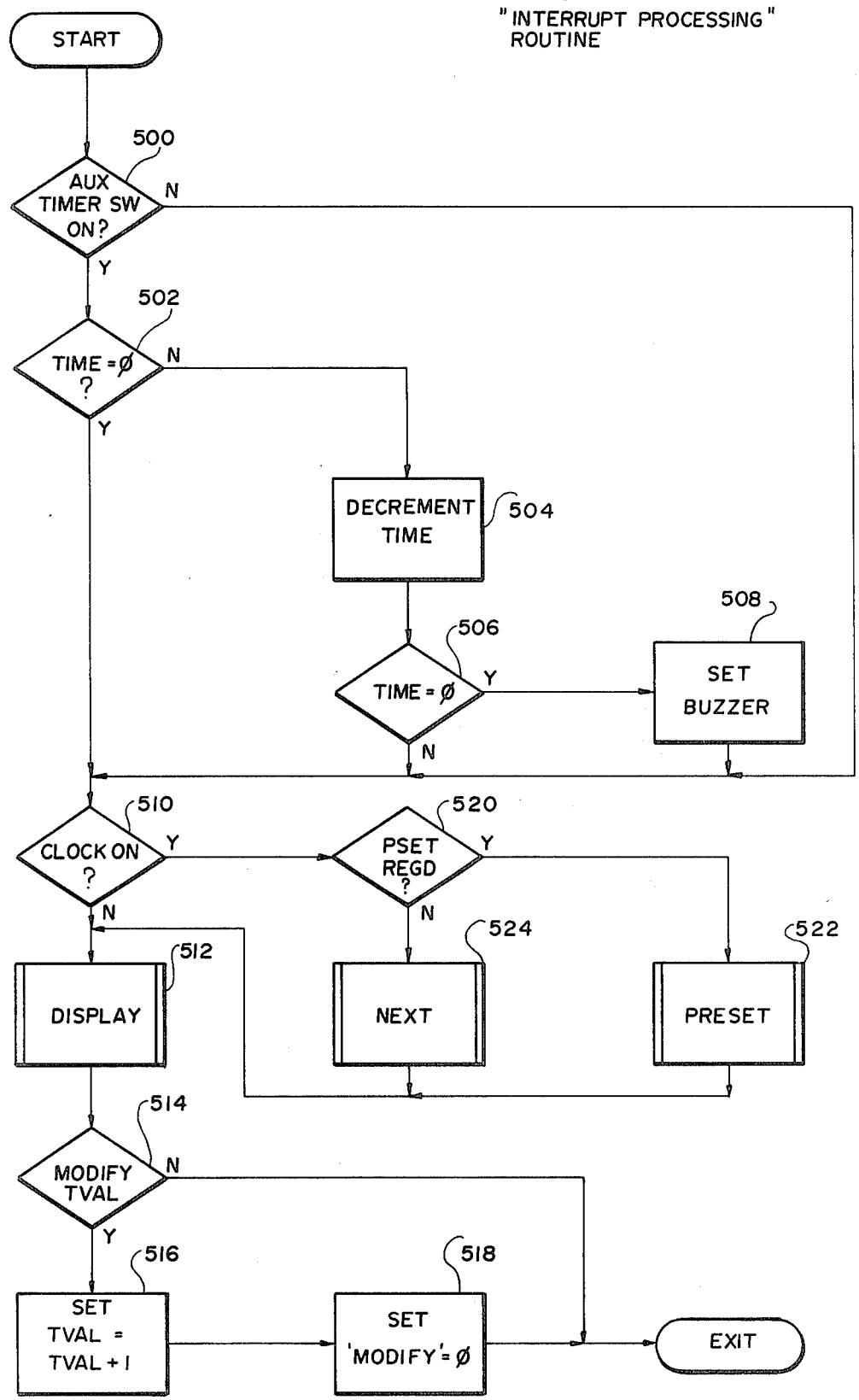

"PRESET" SUBROUTINE

"CHANGE" SUBROUTINE

"DISPLAY" SUBROUTINE

COMPUTERIZED TOMOGRAPHY SYSTEM

CROSS REFERENCE TO RELATED APPLICATION

This invention is related to the tomography system disclosed in U.S. Ser. No. 835,738, filed Sept. 22, 1977, now U.S. Pat. No. 4,139,776, entitled "A System For Circular And Complex Tomography", M. J. Hellstrom, which application is also assigned to the assignee of the present invention. Reference is also made to another related application assigned to the present assignee, which is U.S. Ser. No. 845,132, filed on Oct. 25, 1977, now U.S. Pat. No. 4,145,613 entitled "Motorized X-Ray Tube Assembly", filed in the name of Laverne R. Bunch.

BACKGROUND OF THE INVENTION

This invention relates generally to radiological apparatus and more particularly to means for simultaneously moving elements of an X-ray system in proper synchronism to achieve tomograms without any mechanical linkage between the source and image receptor.

Earlier systems for performing tomographic procedures which included linear, circular, trispiral and other complex motions, for example, required massive and complex precision mechanical linkages between the X-ray beam source and the X-ray receptor which may comprise a film holder or bucky, so that their respective motions can be precisely controlled with regard to the patient or object under examination.

More recently, U.S. Pat. No. 4,087,694, which issued on May 2, 1978, and entitled "Tomography System", by M. J. Hellstrom, et al. and in the above cross-referenced related application, U.S. Ser. No. 835,738, entitled "A System For Circular And Complex Tomography", M. J. Hellstrom, there is described linear and complex tomographic systems which included means for eliminating the conventional mechanical linkage between the overhead tube suspension or bridge and a bucky in an X-ray table. In both instances, measures of components of the position of the X-ray source are determined by means of radiant energy utilizing a laser interferometer. Changes in the position of the X-ray source are electronically scaled to determine the changes which must be made simultaneously to the position of the image receptor, meaning that the X-ray source is first driven and the changes in its position are measured, whereupon the image receptor is moved in a manner related to the measured changes of the position of the X-ray source. Movement in both cases is accomplished by stepper motors and an electronic system for generating pulse sequences for each of the stepper motors. Stepper motor translation of the image receptor is also disclosed in assignee's U.S. Pat. No. 4,095,110 entitled "Means For Stepping X-Ray Receptor In Direction Opposite To Position Change Of Source", which issued on June 13, 1978 in the name of L. R. Bunch.

In addition to the aforementioned systems, one other means is known for performing a tomographic procedure which obviates the need for mechanical linkage between the X-ray source and the receptor. Such apparatus is disclosed in U.S. Pat. No. 3,809,886, entitled "Dynamic Tomography With Movable Table", G. D. Cochran, et al. which issued on May 7, 1974.

SUMMARY

Briefly, the subject invention is an improvement over U.S. Pat. Nos. 4,087,694 4,095,110 and 4,139,776 in that both linear and complex tomographic procedures can be performed while still not requiring mechanical coupling between the X-ray source and the image receptor but it additionally obviates the heretofore required radiant energy sensing of the positional change of the X-ray source.

The improvement is directed to both method and apparatus wherein a movable support assembly containing a tiltable X-ray source are each moved by means of electrical stepper motors and are non-mechanically coupled to an X-ray receptor which is also adapted to be moved by means of a stepper motor coupled thereto for obtaining the tomogram. Each stepper motor is under the precise control of a stored program digital computer which causes respective pulse trains having a predetermined interrelationship to be applied to the three movable elements to control their mutual positions during a tomographic sweep in an open loop mode of operation. Additionally, the computer activates individual self-centering closed loop control circuits for the bridge, source and receptor whereby they are brought into vertical alignment at the end of a tomographic sweep or on command of the operator. Also the computer is adapted to sense completion of the centering operation. It will also cause, on command, the elements depending upon the parameters inputted thereto, to move in proper directions to a calculated reference or preset position and thereafter to make a tomographic sweep. The computer additionally overcomes adverse affects of transient mechanical vibrations in the system by creating a pause to permit the decay of the mechanical vibrations and then controlling the acceleration of the stepper motors to achieve a constant velocity and by initiating the physical sweep at a predetermined time before activating the X-ray source. In the closed loop centering mode, the stepper motors are driven by respective voltage controlled oscillators; however, in the open loop mode each stepper motor receives an independently divided output from a master oscillator. The division factors for source angulation, support and receptor motion are constantly updated at periodic intervals during the control program. The division factors are related to each other by the parameters of the tomographic sweep selected by the operator.

DESCRIPTION OF THE DRAWINGS

FIG. 13 is a flow chart illustrative of the INTERRUPT PROCESSING routine of the control program shown in FIG. 9;

DETAILED DESCRIPTION OF THE PREFERRED EMBODIMENT

Figure 1:
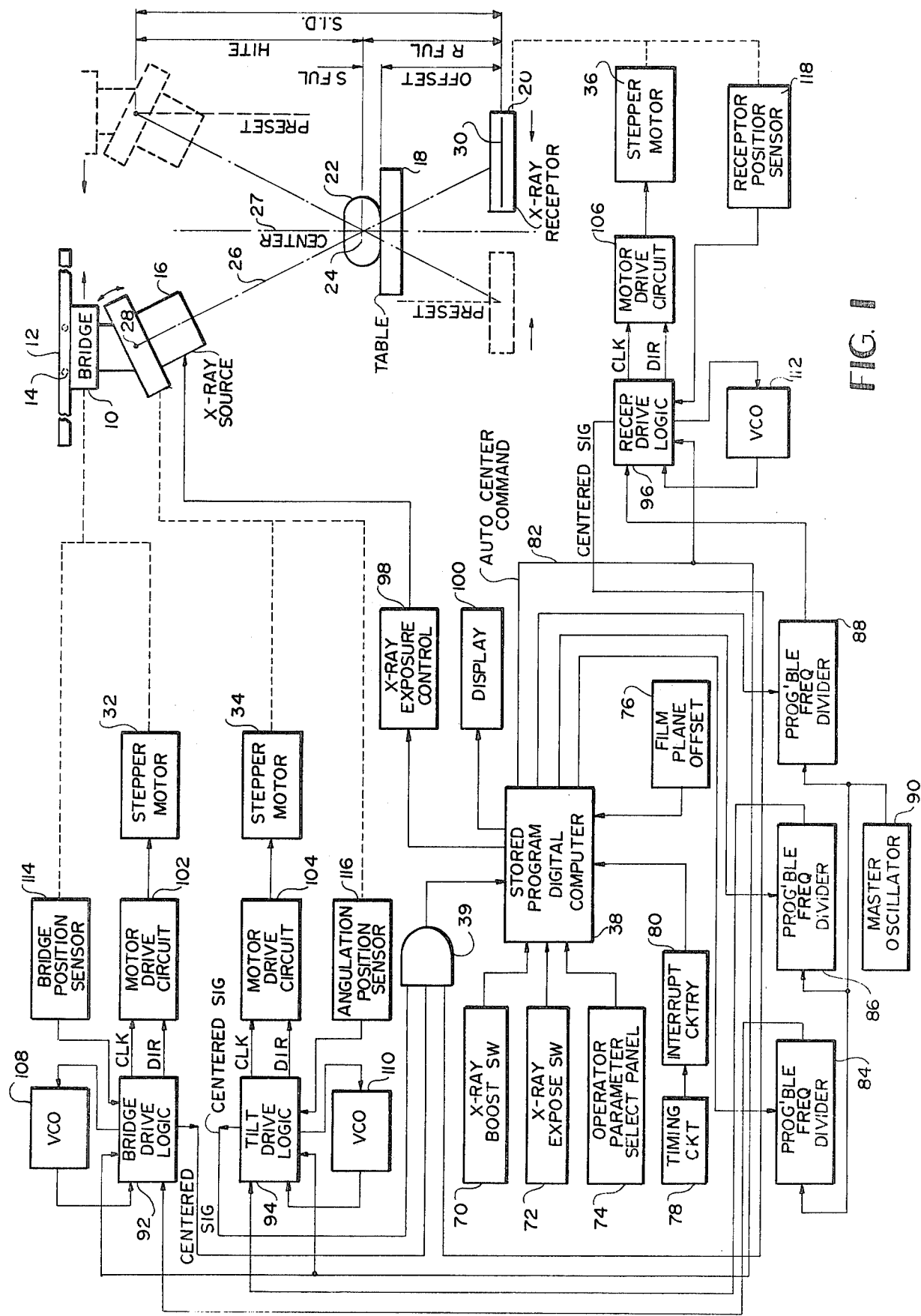
FIG. 1 is a block diagram illustrative of the preferred embodiment of the subject invention.

Referring now to the drawings and more particularly to FIG. 1, reference numeral 10 denotes an X-ray tube suspension system comprising a bridge or tubestand which is mounted for translational movement on a ceiling rail assembly 12 which includes a plurality of rollers 14 or the like. An X-ray assembly including an X-ray tube source 16 is rotatably mounted for variable angulation on the support assembly 10 and is directed through an X-ray table 18 to a movable X-ray receptor assembly 20 consisting of an X-ray film holder commonly referred to as a bucky. Reference numeral 22 denotes a patient or other object under examination. As is well known in a tomographic procedure, the support assembly 10 including the X-ray source 16 and the receptor assembly 20 which contains an X-ray film 30 are moved in a tomographic manner while maintaining a constant point of fulcrum 24 in space within the patient 22 when an X-ray beam 26 emanates from the focal spot 28 and impinges on the surface of an image plane, i.e. the film 30. When the motions of the bridge 10, the source 16 and the receptor assembly 20 are properly aligned and synchronized, a well defined image of the subject at the plane of the fulcrum 24 will be produced on the film 30 while blurring the surrounding image regions.

While the present invention contemplates both linear and complex type of tomography apparatus, a linear type system is presently disclosed by way of explanation, but not limitation since in view of the above referenced prior art circular, spiral or other complex sweeps can be achieved by skill of the art modifications based upon present teachings. Accordingly, each of the three movable elements namely the support assembly 10, the X-ray source 16, and the X-ray receptor assembly 20 are moved, i.e. translated/rotated by means of respective stepper motors 32, 34 and 36 in accordance with conventional practice.

Bearing the foregoing in mind, the inventive concept of the present invention is directed to an improved system of control of the stepper motors 32, 34, 36 by means of a stored program digital computer 38 preferably a microcomputer having a stored operational program or code therein for controlling operation of the system in accordance with operational parameters which have been inputted thereto by an operator.

Figure 2:
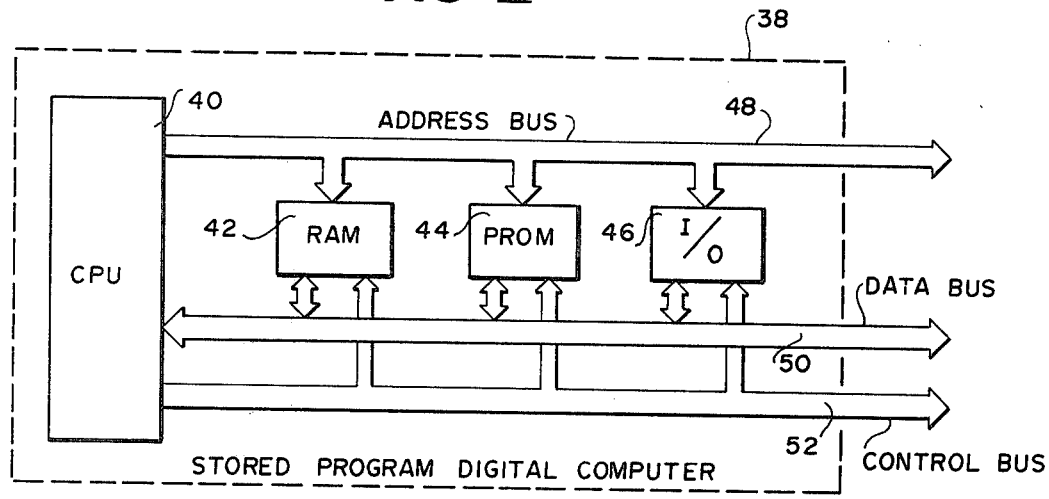
FIG. 2 is a block diagram illustrative of the essential elements of a stored program digital computer.
Figure 3:
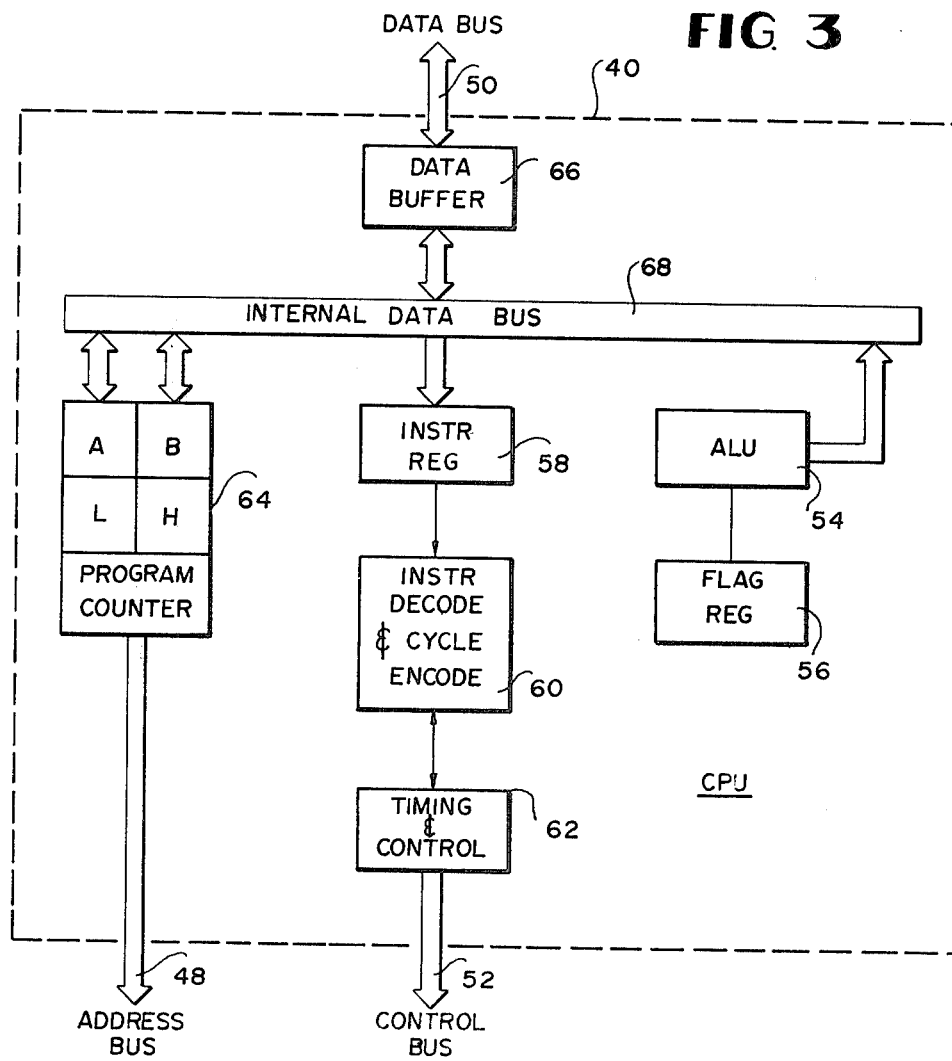
FIG. 3 is a block diagram illustrative of the essential elements of a microprocessor utilized as the central processing unit of the computer shown in FIG. 2.

Prior to discussing the invention in detail, reference is made to FIG. 2. The following general considerations are offered by way of background. Typically, a stored program microcomputer fabricated on semiconductor chips consists of a central processor (CPU) 40, a random access memory (RAM) 42 which is used as a means for storing data, a programmable read only memory (PROM) 44 which serves as a place to store instructions and information that direct activities of the CPU, and a plurality of input/output ports (I/O) 46. The CPU 40 couples to an address bus 48 as well as a bi-directional data bus 50 and a control bus 52. The CPU 40 shown in FIG. 2 as noted above, preferably comprises a microprocessor, a typical example of which is an Intel Corp. 8080 which may be associated with other circuits, as for example, the Pro-Log Corp. 8821 8-bit parallel control processor unit. As is well known, such a micro-processor is made up of the following principal elements as shown in FIG. 3: (1) An 8-bit arithmetic and logic unit (ALU) 54 capable of performing addition, subtraction and comparison, as well as logical operations such as AND, OR, EXCLUSIVE-OR, SHIFT and ROTATE; (2) a flag register 56 which is used to indicate the outcome of a prior ALU operation, such as whether the result was positive, negative or zero; (3) an instruction register 58 which holds the instruction being executed; (4) a unit 60 for interpreting the instruction and controlling the sub-operations necessary to execute the instruction; (5) a timing and control unit 62 for receiving and transmitting control signals from devices external to the ALU; (6) a local storage unit 64 comprising typically four or more 8-bit registers and a program counter which is normally incremented each time instruction is executed and which contains the address of the next instruction to be executed; (7) an address bus which as shown in FIG. 2, comprises the address bus 48, and which typically is a 16-bit wide bus which carries the memory location or other external device location which is to receive data from or transmit data to the micro-processor; (8) a data bus which as noted above consists of the data bus 50 shown in FIG. 2 and is typically an 8-bit wide bus; (9) and a data buffer 66 or latch coupled between an internal data bus 68 and the data bus 50 shown in FIG. 2 and which acts to temporarily hold a word to be sent via the data bus 50 to an external device or received via the data bus from such a device. For a more detailed treatment of stored program digital computers utilizing micro-processors, reference can be made to the September, 1977 issue of *Scientific American*, which provides a detailed technical overview of the current state of the art of "microelectronics".

Accordingly, the stored program digital computer 38 is operable by means of a self-contained instructional code or control program, to be subsequently described, to precisely control the motions of the bridge 10, the X-ray source 16 and the X-ray receptor assembly 20 by means of computer controlled interrelated pulse trains applied to the respective stepper motors 32, 34 and 36.

Referring back now to FIG. 1, the computer 38 in addition to having a manually operated X-ray BOOST switch 70 and an X-ray EXPOSE switch 72 coupled thereto, has an operator parameter select switch panel 74 which contains a plurality of manually operable switches, not shown, having the following designations, which will become evident as the following description proceeds; TOMO ON, CENTER, TEST, UP, DOWN, CLOCK ON/OFF, DISPLAY TIME, 8°-SLOW, 8°-FAST, 30°-SLOW, 30°-FAST, 45°-SLOW, and 45°-FAST. Also a multi-bit digital switch 76 is coupled to the computer 38 which is adapted to input a parameter to the computer indicating the distance between the top of the X-ray table 18 and film 30 of the X-ray receptor 20 assembly and is referred to hereinafter as OFFSET. This parameter is subject to change and is one which is normally set during initial system installation. The computer 38 is adapted for operation in a well known interrupt processing mode and accordingly is coupled to a timing circuit 78 through interrupt circuitry 80 which is adapted to scale a 50/60 Hz reference signal to 50 millisecond timing pulses which activate the interrupt processing intervals to be described. The input ports, not shown, of the computer 38 additionally receive a composite digital feedback signal from an AND gate 39 corresponding to a "Centered" condition of the support assembly 10, the X-ray source 16 and the X-ray receptor assembly 20 via an AND gate 39. This feedback signal occurs at the completion of a self-centering procedure initiated by the computer outputting a command through an output port on AUTO CENTER COMMAND signal lead 82.

Output ports of the computer 38 are coupled to three programmable frequency dividers 84, 86 and 88, which are adapted to scale down the frequency of the output of a master oscillator 90 and to feed, respectively, a bridge drive logic circuit 92, a tilt i.e. angulation drive logic circuit 94, and a receptor drive logic circuit 96. Additionally, the output ports of the computer are coupled to an X-ray exposure control circuit 98 and a visual display unit 100.

Three separate stepper motor drive units are provided, as evidenced by the block diagram in FIG. 1, by having respective stepper motor drive circuits 102, 104 and 106 coupled to the stepper motors 32, 34 and 36 through the respective drive logic circuits 92, 94, 96. The three drive logic circuits are adapted to feed clock pulses (CLK) and a direction signal (DIR) to the respective motor drive circuits. The system drives in at least two modes defined as auto-centering and tomo sweep. In the auto-centering mode, the three elements of the system drive to "Center" by means of three separate voltage controlled oscillators 108, 110 and 112, coupled in closed loop positioning servo sub-systems through the respective drive logic circuit 92, 94 and 96, while in the tomo sweep mode motions are accomplished through open loop computerized control of the frequency divider circuits 84, 86 and 88, which have their outputs respectively coupled via line drivers to the drive logic circuits 92, 94 and 96.

In order to provide the closed loop centering control of the bridge 10, the X-ray source 16 and the X-ray receptor 20, respective position sensor units 114, 116 and 118 are coupled into the respective drive logic circuits to control the associated voltage controlled oscillators 108, 110 and 112.

Figure 4:
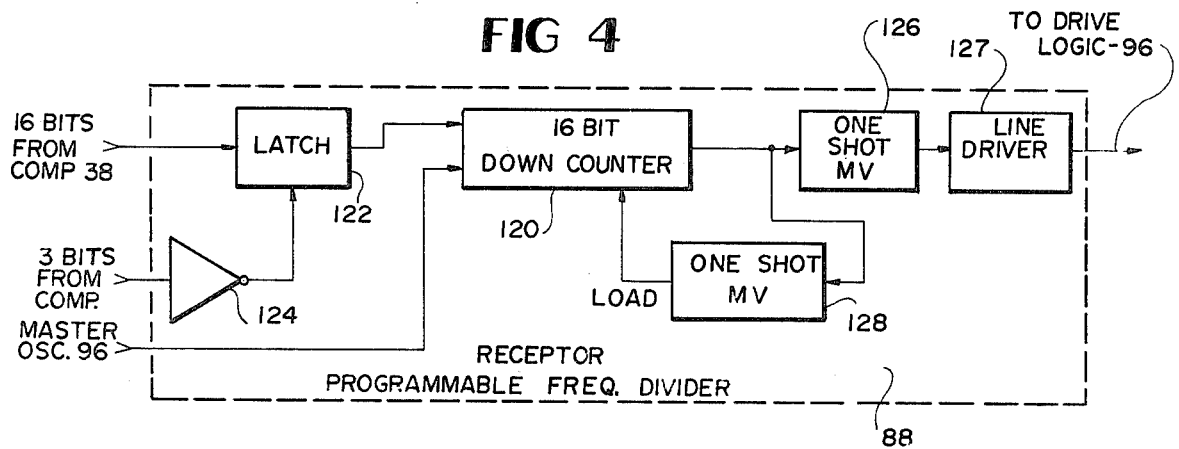
FIG. 4 is an electrical block diagram typically illustrative of the programmable pulse frequency dividers shown in FIG. 1.
Figure 5:
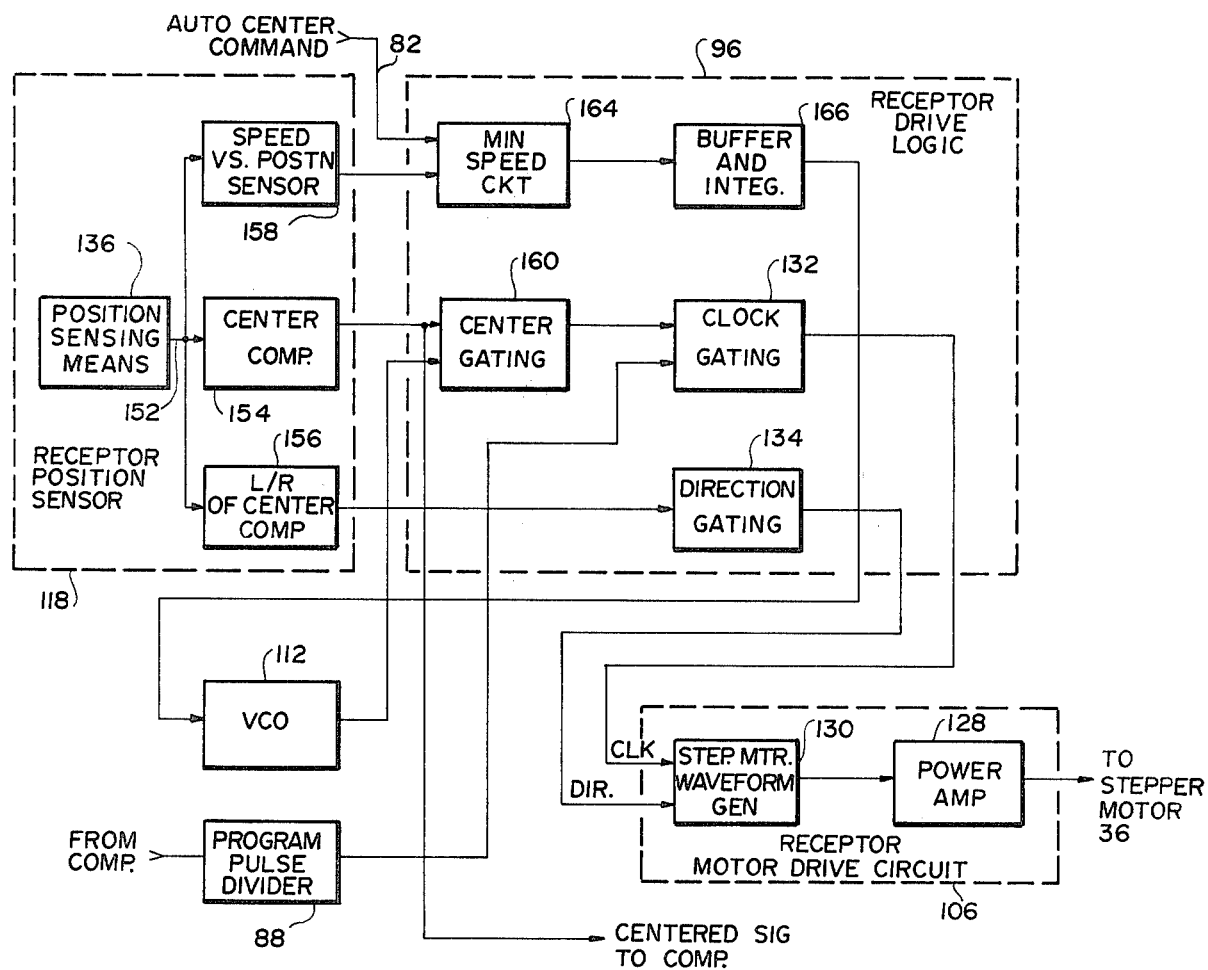
FIG. 5 is an electrical block diagram illustrative of a position sensor, drive logic and motor drive circuit configuration for one stepper motor as shown in FIG. 1.
Figure 6:
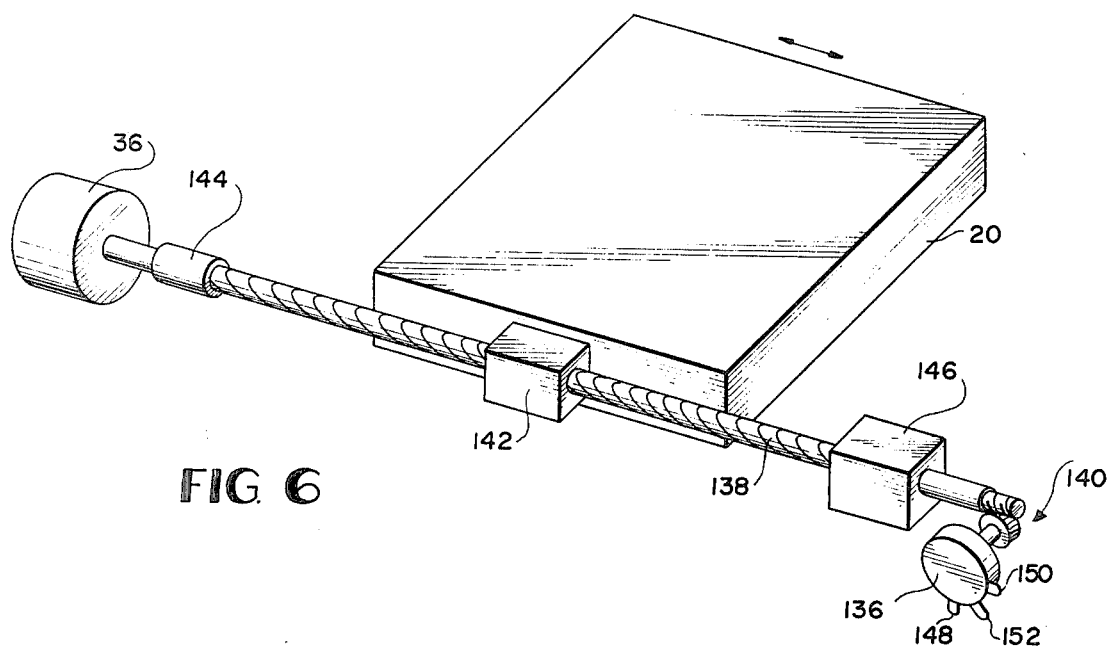
FIG. 6 is an electrical-mechanical diagram illustrative of the position sensor arrangement for the X-ray receptor.

Further detail is provided in FIGS. 4–6. FIG. 4, for example, is illustrative of one of the three frequency dividers 84, 86 and 88 which are identical. Since all three are identical, only the frequency divider 88 will be considered. The basic element in each frequency divider is a 16-bit programmable down counter circuit 120, which has its count set by means of a binary latch 122 which is loaded with a 16-bit binary word corresponding to a desired value outputted from the output ports of the computer 38. The 16-bit word appears on a bus connected to the latches 122 of each of the three frequency dividers 84, 86 and 88. A 3-bit address circuit 124 is coupled to the latches which when addressed, causes the appropriate latch to store the desired count. The count is loaded into the down counter 120 on command whereupon the frequency output of the master oscillator 90 is effectively divided to couple pulses at a predetermined rate to the drive logic. One shot multivibrators 126 and 128 are utilized to pulse shape and couple the down counter to the drive logic and to command the loading of the count from the latch 122 into the down counter 120.

The computer 38 then is operable to consecutively alter the divider factor of each down counter in the three frequency divider circuits 84, 86 and 88 at periodic intervals, i.e. every 50 milliseconds (interrupt processing interval), to provide precisely controlled displacements of the support assembly 10, the X-ray source 16 and X-ray receptor assembly 20. Each of the frequency dividers then provide respective pulse trains, which by the means described above are controlled to obtain desired motion characteristics such as, for example, the total angular displacement of the line joining the center of the film 30 and the focal spot 28 relative to a central axis 27 normal to the plane of the image receptor assembly during which the tomographic exposure is obtained.

Noting that the programmable frequency divider 88 for the receptor feeds to the receptor drive logic 96, reference is now made to FIG. 5 which illustrates that the stepper motors or in this instance the receptor stepper motor 36 is driven from the motor drive circuit 106 by either the output of the programmable frequency divider 88 or its respective voltage controlled oscillator 112 depending upon whether the system is being centered i.e. in the auto-centering mode or is in the process of making a tomographic i.e. in the tomo sweep mode. The motor drive circuit 106 typically is comprised of a power amplifier 128 and a stepper motor waveform generator 130 which is adapted to generate the appropriate pulse waveform sequence in response to the clock signal and directional signal coupled thereto from a clock gating circuit 132 and a direction gating circuit 134. In the tomo sweep mode, the clock gating circuit is responsive to the output of the programmable pulse divider 88; however in the centering mode, it is responsive to pulses generated by the VCO 112.

As is well known, a stepper motor can provide very precisely controlled displacements. However, in order to precisely control the absolute position of an object, it is necessary to rely on some type of position reference. In the present invention the support assembly 10, the X-ray source 16, and the receptor assembly 20 are first caused to move to a "center" position along the axis 27 shown in FIG. 1 by a closed loop circuit configuration including respective position sensing means. Illustratively, the sensing of the position of the receptor assembly 20 during "centering" is accomplished by means of a potentiometer 136 as shown in FIG. 6 which is mechanically coupled to a ball screw shaft 138 driven by means of the stepper motor 36 through a worm and gear assembly 140. The X-ray receptor assembly 20 is shown comprising a bucky type of receptor having mechanically coupled thereto a ball screw nut 142, which engages the shaft 138. The elements 144 and 146 designate a mechanical coupling and a bearing block respectively. A supply potential, not shown, is applied across terminals 148 and 150 and accordingly a voltage appears at terminal 152 which is a measure of the position of the bucky type receptor assembly 20.

Referring again now to FIG. 5, three circuits 154, 156 and 158 are responsive to the magnitude of the position voltage to perform the three separate functions. The circuit 154 comprises a pair of level sensors which may be, for example, a Schmitt trigger circuit or the like, which outputs a signal when the input is within a predetermined range about a reference e.g. $\frac{1}{2}$ V where V is the voltage applied across terminals 148 and 150. Accordingly, the comparator circuit 154 is a center sensor and outputs a control signal at the "center" position of the receptor 20. The circuit 156 comprises a similar voltage comparator providing an output indicative of the position of the receptor 20 depending on whether it is left or right on the "center" position. The sensor circuit 158 on the other hand is responsive to the magnitude of the voltage at terminal 152 to indicate simply whether the receptor is far or near the "center" position, the reason being that it is desirable in the self-centering mode to drive the stepper motors at a relatively higher rate when the receptor is relatively far away from the "center" position, but at a slower rate as the receptor nears the "center" position. This is due to the fact that stepper motors can be precisely stopped when running slowly and it is desirable to stop the stepper motor 36 exactly at the "center" position.

Accordingly, the circuit 156 controls the direction gating circuit 134 causing pulses of one sequence or another to be generated by the waveform generator 130 while the center comparator 154 controls a center gating circuit 160 which permits the pulse output of the VCO 112 to be coupled to the clock gating circuit 132 only until such time that centering has occurred. When all motions are centered, the clock gating circuit 132 is adapted to receive pulses from the computer controlled frequency divider circuit 88. The sensor circuit 158 is coupled through a minimum speed circuit 164 which guarantees a minimum voltage value which is coupled to the VCO 112 through a buffer and integrator circuit 166. In operation, the minumum speed circuit 164 receives an enabling signal in the form of an AUTO CENTER command signal from the computer 38 when a centering of the receptor assemlby 20 is required, whereupon the sensor circuit 158 will cause a relatively higher or lower frequency pulse train to be produced by the VCO 112, depending upon the relative position of the receptor assembly 20 from the center position but never at a frequency lower than a predetermined minimum value. When the center position is reached, the center gating circuit 160 inhibits the VCO pulse train from being coupled to the clock gating circuit 132. The stepper motor waveform generator now will receive a pulse train coupled from the frequency divider circuit 88 to the clock gating circuit 132.

Figure 7:
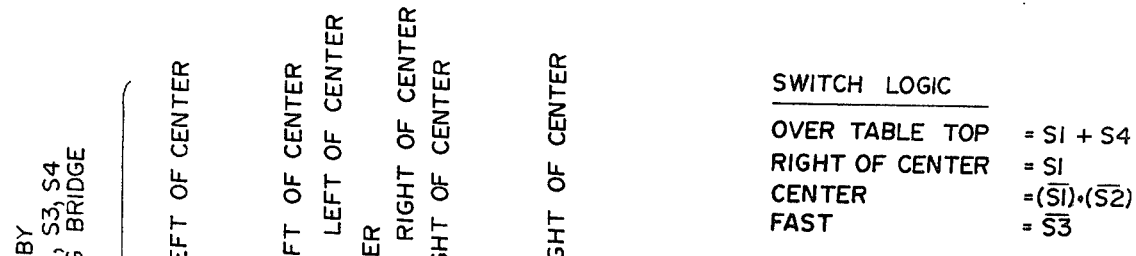
FIG. 7 is a diagram illustrative of the multiple switch arrangement for sensing the position of the bridge shown in FIG. 1.

The drive logic circuitry for the bridge 10 is essentially the same except that the position sensor therefor consists of four mechanically operated switches, not shown, mounted on the bridge but which are adapted to be operated for various travel lengths of the bridge. Diagrammatically, this is illustrated in FIG. 7 which additionally includes a logic table indicating now various logic signals are related to switch closures.

It can be seen then that the basis for the start of operation of the overall system involves independent self-centering of bridges 10, the receptor 20, and the angular position of the X-ray source 16, and in each case it is only necessary to sense whether the specific element is left or right of "center", whether it is near or far from "center" and whether it is within a prescribed range within which centering action is permitted and finally whether it is on "center" or not. If the element, i.e. the support assembly 10, the receptor assembly 20, or angulation of the source 16 is within the range permitting automatic centering, then the right or left sensing determines the direction of rotation of the respective stepper motor. If the element is relatively far from "center", the appropriate voltage control oscillator generates pulses at a relatively high frequency in order to move the element rapidly towards "center". When the element is sensed to be near "center", the VCO generates pulses at a lower frequency, and more particularly one which considering the mass of the element to be stopped can be abruptly terminated without loosing synchronism with the motor, so that it will be easier to stop the motion when "center" is reached. When "center" position is reached, the VCO pulses are terminated and the element comes to rest. As can be seen from FIG. 1, "center" comprises alignment of the three elements along the axis 27.

Once the elements have been "centered" they are next displaced under computer control to a predetermined "preset" or "start" position (FIG. 1) by means of respective pulse trains generated by the master oscillator 90 and appropriately divided in frequency by the respective programmable frequency dividers 84, 86 and 88. It should be pointed out that the "preset" position commanded depends on the fulcrum height and the angle of the tomographic sweep which the operator has selected as well as other mechanical and electrical requirements of the system such as the torque speed characteristics of the motors, the system masses and friction. The operational control routine of the computer 38 to be described with reference to FIGS. 9 through 17 calculates the requirements to make the aforesaid displacement of the elements to their respective "preset" position and thereafter controls the generation of three pulse frequency divider factors to make a tomographic sweep. After a predetermined acceleration period the three stepper motors 32, 34 and 36 begin a constant velocity period of motion and a short time later the computer controls the energization of the X-ray source, thereafter terminating X-rays at the end of the inputted exposure time.

Figure 8:
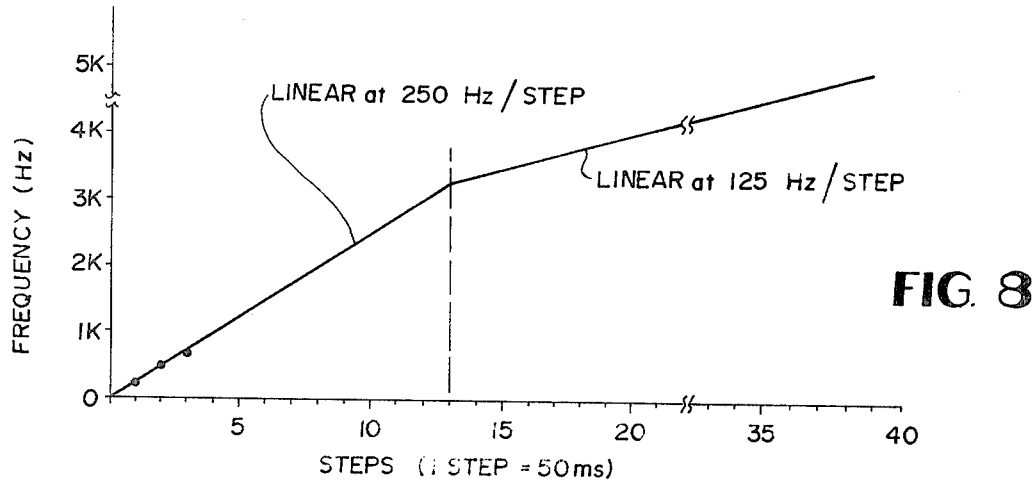
FIG. 8 is a graph illustrative of the acceleration characteristic provided by the stepper motors of the subject invention.

Since stepper motors are characterized by a generally falling torque-speed characteristic, in order to provide maximum acceleration to a mechanical mass, it is desirable to move along an operating path which does not exceed this curve, but which provides maximum torque at all speeds. Such a curve, i.e. a straight line the torque (acceleration)-speed plane which is a straight line with negative slope corresponds to an exponential relationship between speed and time. Since stepper motor velocity is proportional to the frequency of the pulses supplied thereto, it is desirable to provide a train of pulses whose frequency varies exponentially with time. In the present invention, however, this is approximated by two straight line segments as shown in FIG. 8. This characteristic is implemented by storing a velocity table shown below providing discrete frequency divider values and pulse counts in a plurality of separate memory cells in the PROM 44 shown in FIG. 2 which can be selectively accessed by a pointer in a manner well known to those skilled in computer technology. For example, where cell 1 of 31 cells stores zero values and where the output frequency of the master oscillator 90 is 4 MHz, the divider values of the cells 2-14 increase count output in increments of 12 or 13 pulses or 250 Hz per step. However, for the cells 15-31, the counts increase in increments of 6 or 7 counts per step or 125 Hz per step.

VELOCITY TABLE

| Cell No. | Divider VAL-TDIV | Counts-CCNT | Frequency -Hz |
|---|---|---|---|
| 1 | 0 | 0 | 0 |
| 2 | 16000 | 13 | 260 |
| 3 | 8000 | 25 | 500 |
| 4 | 5330 | 37 | 740 |
| 5 | 4000 | 50 | 1000 |
| 6 | 3200 | 63 | 1260 |
| 7 | 2667 | 75 | 1500 |
| 8 | 2286 | 87 | 1740 |
| 9 | 2000 | 100 | 2000 |
| 10 | 1778 | 113 | 2260 |
| 11 | 1600 | 125 | 2500 |
| 12 | 1455 | 137 | 2740 |
| 13 | 1333 | 150 | 3000 |
| 14 | 1231 | 163 | 3260 |
| 15 | 1157 | 173 | 3460 |
| 16 | 1113 | 180 | 3600 |
| 17 | 1074 | 186 | 3720 |
| 18 | 1039 | 192 | 3840 |
| 19 | 1006 | 199 | 3980 |
| 20 | 976 | 205 | 4010 |
| 21 | 947 | 211 | 4220 |
| 22 | 920 | 217 | 4340 |
| 23 | 894 | 224 | 4480 |
| 24 | 870 | 230 | 4600 |
| 25 | 847 | 236 | 4720 |
| 26 | 825 | 242 | 4840 |
| 27 | 804 | 249 | 4980 |
| 28 | 784 | 255 | 5100 |
| 29 | 765 | 261 | 5220 |
| 30 | 748 | 267 | 5340 |
| 31 | 731 | 274 | 5480 |

Accordingly, the computer 38 is adapted to access any of the 31 cells in either an ascending, descending or repetitive sequence to effect a synchronized movement of the support assembly 10, source 16 and receptor assembly 20 as directed by the operational code or control program which is outlined in routine form by flow charts shown in FIGS. 9-17. However, before discussing these figures in detail, mention should also be made of the fact that the fulcrum height, i.e. the location 24 as shown in FIG. 1, is determined and controlled by the ratio of the frequencies of the pulse train applied to the stepper motors driving the support assembly 10 and X-ray receptor assembly 20, respectively, and can be expressed as follows:

$$FH = \frac{S.I.D.}{1 + \frac{v_b}{v_r}} \quad (1)$$

where FH is the fulcrum height, S.I.D. is the distance between the focal spot 28 and the film 30 and $v_b$ and $v_r$ are the respective velocities of the support assembly 10 and the receptor assembly 20. However, the velocities $v_b$ and $v_r$ are proportional to the frequencies $f_b$ and $f_r$ of the pulse trains applied to the stepper motors 32 and 36 and accordingly and the fulcrum height can be expressed as:

$$FH = \frac{S.I.D.}{1 + K} (f_b/f_4) \quad (2)$$

where K is a constant.

Accordingly, by varying the ratio $f_b/f_r$, the fulcrum height FH can be changed as needed in clinical diagnostic procedures. This fulcrum height is selected by the operator as the distance SFUL shown in FIG. 1. However, the system must take into account the OFFSET distance shown in FIG. 1 which is due to the plane of the film 30 being below the patient supporting surface of the table 18 and accordingly, the computer 38 utilizes the parameter RFUL=OFFSET+SFUL in the following control algorithm.

Turning now to the tomo sweep mode which can best be explained in terms of the instruction code in the PROM 44 of the stored program digital computer 38, the system during this mode runs in a loop by means of a set of instructions which repeatedly tests the plurality of manually operable switches on the operator parameter select panel 74 and branches to a particular subroutine whenever one of the switches is operated or whenever a scan is in progress. Simultaneously with this, periodic interrupt processing takes place which actually modifies stepper motor operation. During the time that a scan is in execution, further testing of the switch panel is inhibited by the code and any attempt to operate any control other than the one controlling the sweep will produce no result.

Figure 9:
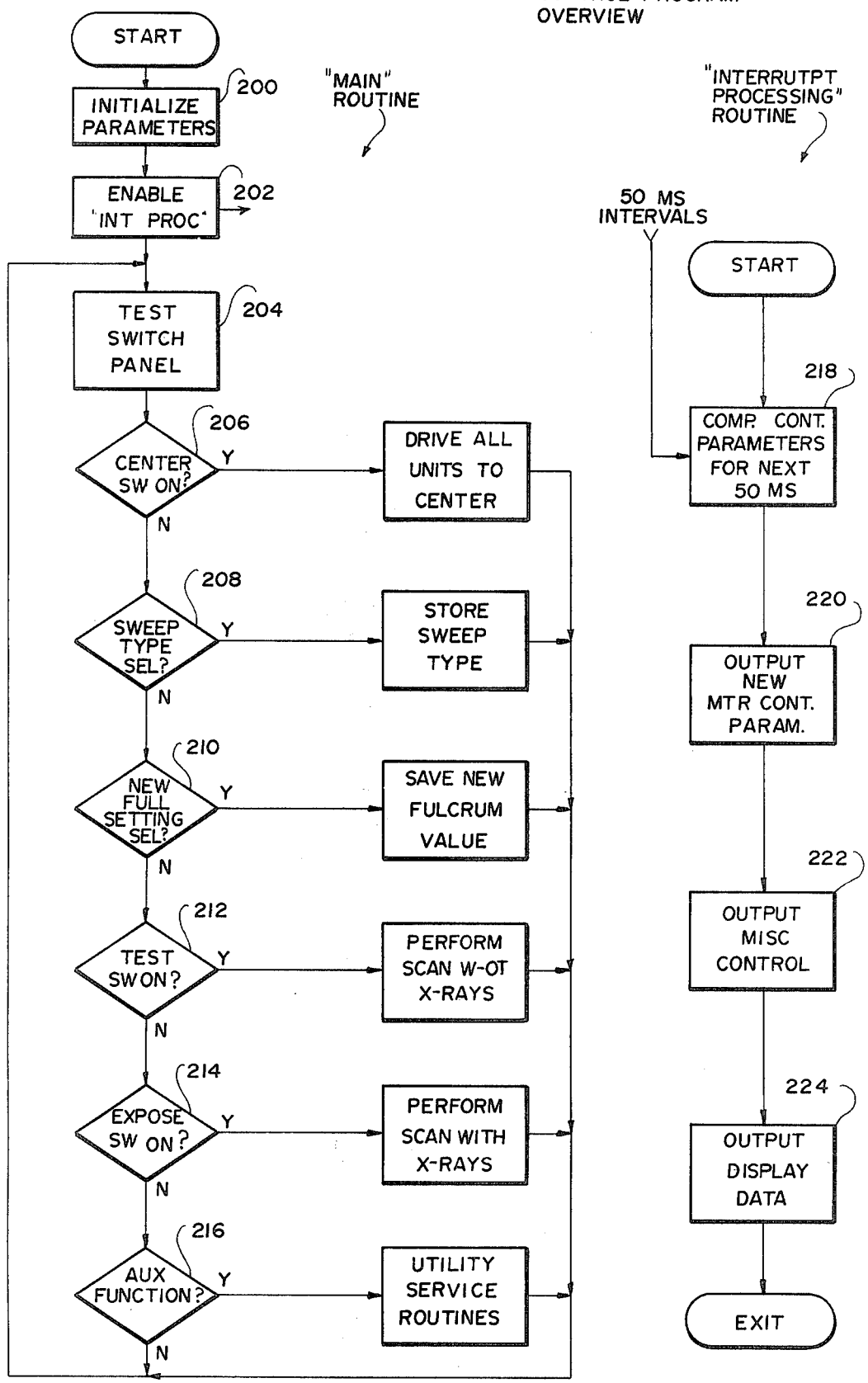
FIG. 9 is illustrative of a flow chart providing an overview of the control program or code stored in the digital computer shown in FIGS. 1 and 2.

Reference is now made to FIG. 9 which discloses an overview of the control program stored in the computer 38. The instructions are contained in two parallel codes, a MAIN routine and an INTERRUPT PROCESSING routine, which are adapted to be carried on simultaneously. The MAIN routine generally may be described as a routine for performing housekeeping and/or bookkeeping functions whereas the INTERRUPT PROCESSING routine acts to refresh or update the programmable pulse frequency divider values of elements 84, 86 and 88 (FIG. 1) at 50 millisecond intervals for direct management of the tomographic sweep or scan once self-centering of the bridge 10, the X-ray source 16 and the X-ray receptor 20 has been completed.

The MAIN routine begins by initializing the input parameters designated by reference numeral 200, which consists of a section of code which assures that there are no values of variable parameters set in the RAM memory 42. Next the INTERRUPT PROCESSING routine is enabled in step 202 and a sequential test 204 is made of the switch panel 74 (FIG. 1) to see which, if any, of the switches referred to above have been activated, i.e. turned on, and based on what is sensed, a subroutine is entered into which, having been completed, makes the next test in the loop. For example, a test is first made in step 206 to determine whether or not the CENTER switch is on. If the answer is affirmative, the AUTO CENTER command is given to drive the three units i.e. the support assembly 10, source 16 and X-ray receptor assembly 20 to "center." Next a test is made at 208 to determine whether or not a desired sweep type has been selected for which if one has been made, the type of sweep is stored in memory. Following this a test 210 is made to determine whether or not a new fulcrum setting has been selected because if none has been made, the previous setting will be retained. If a new fulcrum setting has been made, this value is entered into memory and the routine goes on to the next step 212 to determine whether or not the TEST switch on the panel 74 (FIG. 1) has been activated. If so, a command is given to perform a tomo sweep without X-rays. If the TEST switch is off but the EXPOSE switch is on, this condition is tested at step 214 whereupon a command to perform a tomo sweep with X-rays is given. Following this, a final test 216 is made to determine whether or not auxiliary functions are necessary, in which case utility service routines are entered. Once the INTERRUPT PROCESSING routine has been enabled, an interrupt signal appears at 50 millisecond intervals, at which time a computation step 218 is made to compute the system control parameters for the next 50 milliseconds. The new control parameters are outputted in step 220, followed by outputting miscellaneous control functions in step 222. Lastly it outputs display data in step 224 and then recycles.

Figure 10A:
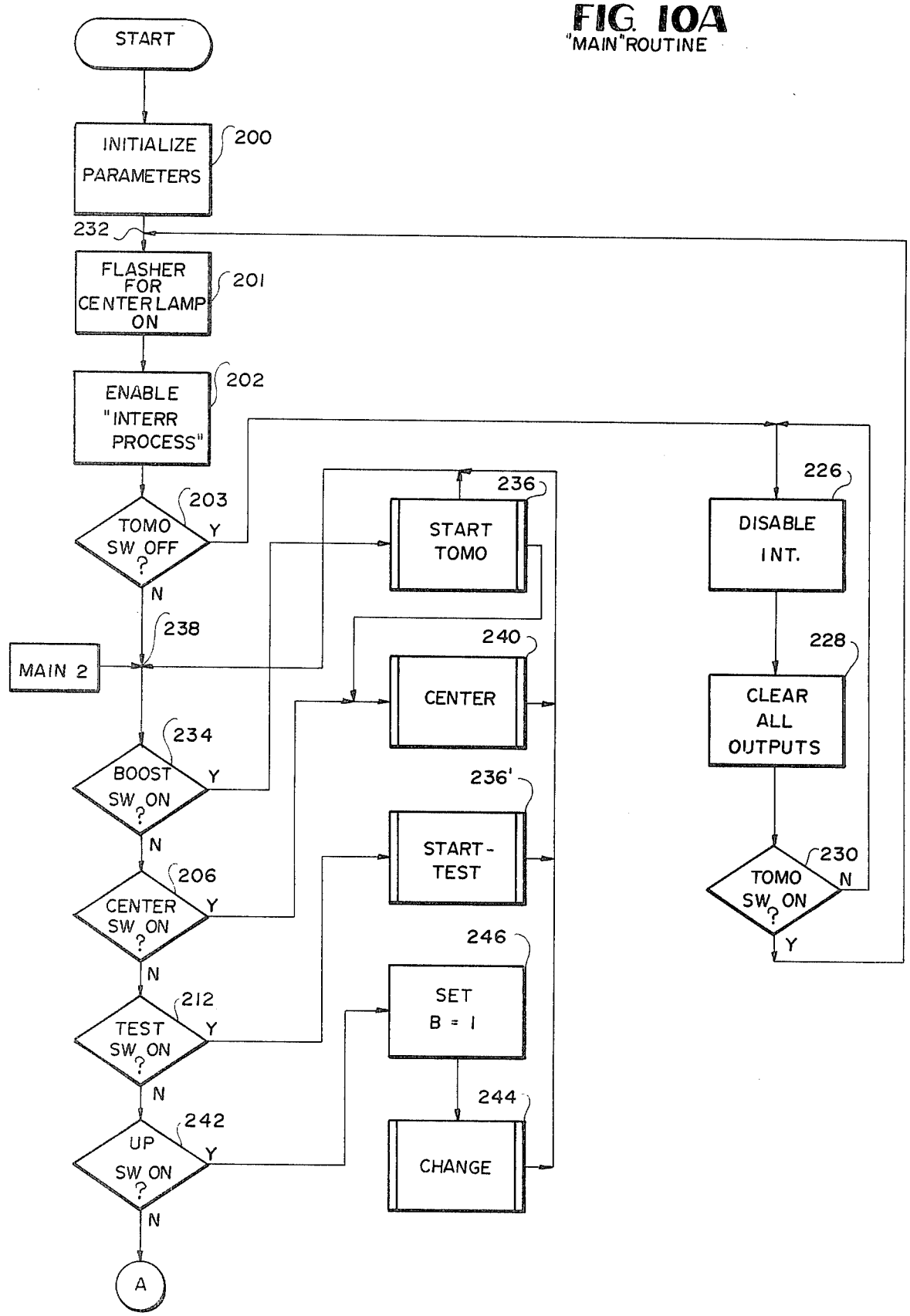
FIGS. 10A and 10B comprise a flow chart illustrative of the MAIN routine of the control program shown in FIG. 9.
Figure 10B:
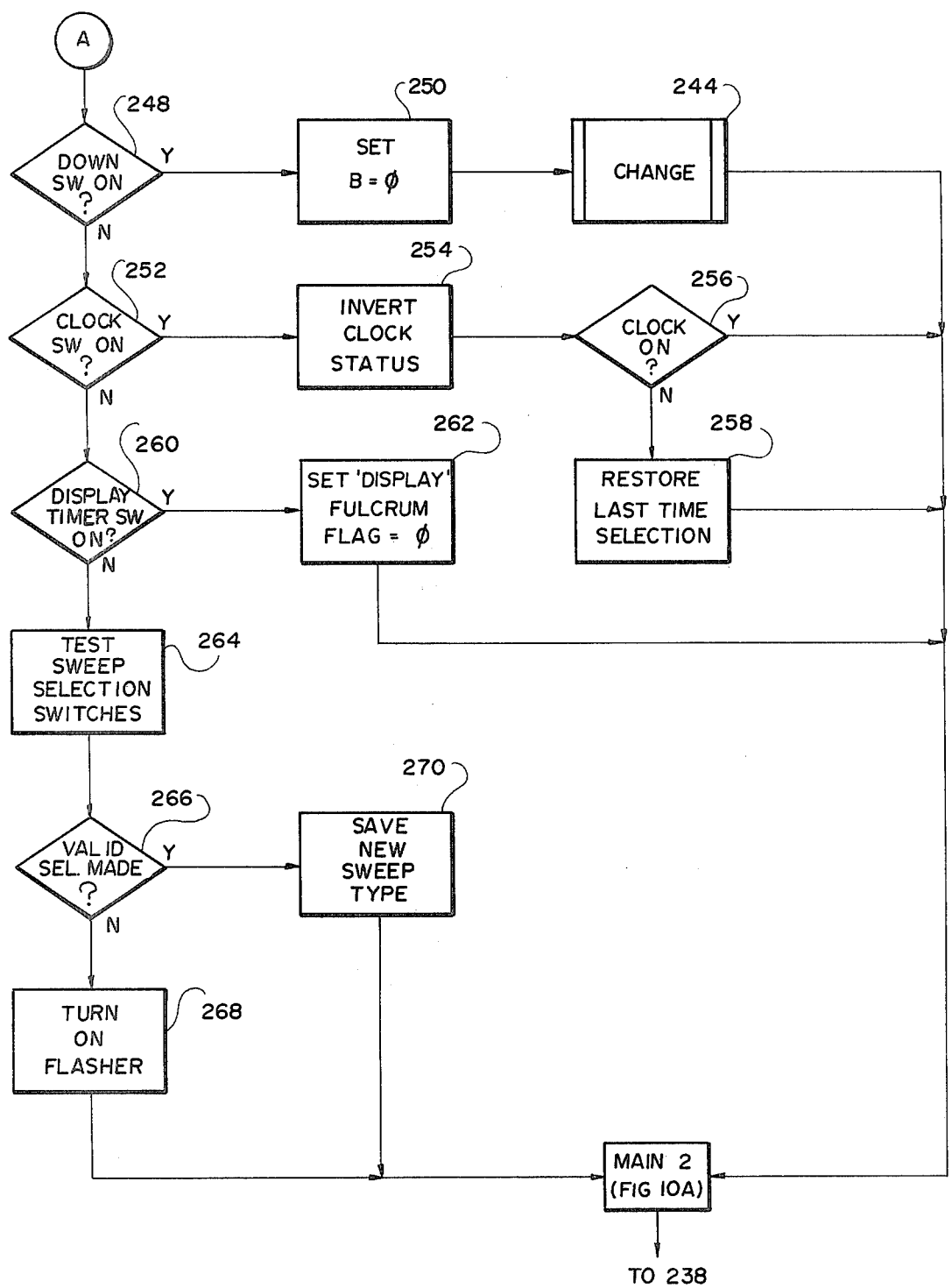

The MAIN routine is illustrated in greater detail by the flow chart shown in FIGS. 10A and 10B and is adapted to branch off into three subroutines identified as CENTER, START TOMO and CHANGE. The INTERRUPT PROCESSING routine is shown in greater detail in FIG. 14 and is adapted to branch off into three subroutines identified as PRESET, NEXT, and DISPLAY.

Referring now to the flow chart of the MAIN routine shown in FIG. 10A, again the step of initializing the parameters 200 is shown but intermediate the step 202 of enabling the INTERRUPT PROCESSING routine 202, the step 201 of turning on the flasher for the "CENTER" lamp occurs. Next a test of the TOMO ON switch on the front panel 74 is made to determine whether it is off as designated by reference numeral 203. If it is off, it will branch into a side routine, which temporarily disables the INTERRUPT PROCESSING routine in step 226, clears all the outputs in step 228, and begins a loop which retests the TOMO ON switch at step 230 to see if it has been turned on. As long as the TOMO ON switch is off, it remains in this loop and keeps recycling until the TOMO ON switch is finally turned on, at which time the routine returns to an entry point 232, whereupon it will immediately proceed to step 234 to see whether or not the BOOST switch 70 (FIG. 1) has been activated. If the BOOST switch 70 is ON, the program branches into the START TOMO subroutine 236, wherein all the computations necessary to execute a sweep or scan are made. The START TOMO subroutine is shown in FIGS. 12A and 12B and will be considered in turn; however, the START TOMO subroutine initially makes a check to determine if the EXPOSE switch 72 (FIG. 1) is also activated so that X-rays can be taken, and at the completion of the procedure, returns to point 238 in the program. If the BOOST switch 70 is not on, the CENTER switch test 206 referred to above is again made and the program branches off into the CENTER subroutine 240 shown in detail at FIG. 11.

Figure 16:
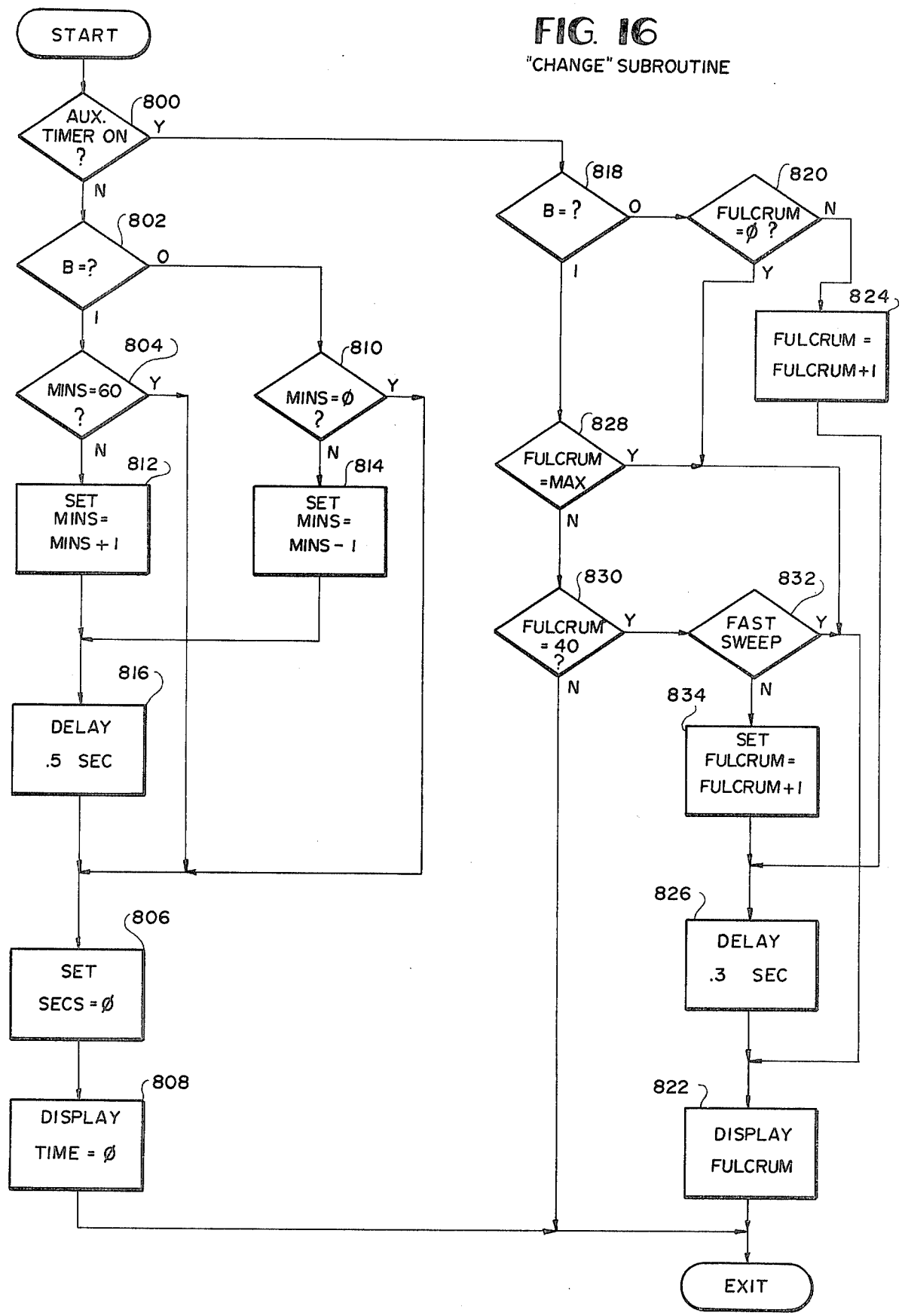
FIG. 16 is a flow chart illustrative of the CHANGE subroutine shown in FIG. 10A.

There is an implicit priority in the MAIN routine in that if two switches were to be activated at once, the system picks the first switch it finds and acts accordingly. If the tests 203, 234, 206 have been negative, the TEST switch test 212 is made and found on, a modified START TOMO routine 236' is initiated, however, without the production of X-rays. The subject system as noted earlier includes two switches on the panel 74 labeled UP and DOWN, which are used to control the data appearing on the display 119 and are used to select an auxiliary timer duration or a desired fulcrum level. If the auxiliary timer is running, it is assumed that it is desired to have a change in the fulcrum setting. Conversely, if the timer is not running, it assumes that a change in time is desired. Both of these functions are accomplished by the CHANGE subroutine 44 as shown in FIG. 16. Accordingly, if the UP switch is activated, the test 242 sets a binary value "1" indicating an increment in a control register "B" by step 246 and then branches to the CHANGE subroutine 244. If the DOWN switch is activated reference to FIG. 10B indicates that if step 248 is affirmative, the "B" register is set to a binary "0" indicating a decrement in step 250 and exits to the CHANGE subroutine 244, which after it has been completed, returns back to the point 238 via MAIN 2. Accordingly, if the operator is holding either the UP or DOWN switch closed, time or fulcrum value will be incremented in two minute steps per second or three half centimeter steps per second, whatever the case may be for each pass back through the entry point 238.

A CLOCK ON/OFF switch is also included on the panel 74 (FIG. 1) and is adapted to change the status of the display from time to fulcrum, and vice versa. Accordingly, the program next tests the CLOCK ON/OFF switch in step 252 which if it is activated and subsequently released, causes an inversion of the auxiliary timer status in step 254, meaning that if the timer is currently running, it is turned off but if it is currently off, it is turned on. The auxiliary timer is essentially an operator selectable stop-watch type of device that is part of the control panel function and which is adapted to display time for the operator up to 60 minutes. If the auxiliary timer is on as evidenced by step 256, the program returns back to entry point 238. All that has been accomplished is turning the auxiliary timer on if it were off. If on the other hand the auxiliary timer was on and it is now off, the routine at this point restores the last time selection by step 258. This means that if the operator for example had set it for a ten minute time delay, and inadvertently stopped the auxiliary timer, the clock will automatically be set back to ten minutes. This has no relationship at all to tomographic operation, it is simply a clock device for use by the operator.

Additionally, the front panel 74 includes a DISPLAY TIME switch which is utilized in the event that fulcrum is presently being displayed and it is desired to obtain a reading of time. When this switch is operated, the routine enters step 260 and tests whether or not the switch is on. If the switch is operated, a flag in the system is temporarily changed which allows time to be displayed instead of fulcrum and it will be displayed as long as the DISPLAY TIME switch is held in an activated position. When the operator releases the switch, the flag is automatically reset to whatever it was before and if fulcrum were being displayed, it will be displayed again and the program reverts back to entry point 238 via MAIN 2.

Following this, the six sweep selection switches 8°-SLOW, 8°-FAST, 30°-SLOW, 30°-FAST, 45°-SLOW and 45°-FAST are tested in step 264. A test 266 is next initiated to see if a valid selection is made under predetermined rules and involves a somewhat complex test. Most of the complexity centers about the fact that each angle has a fast and a slow mode. The fast sweep is not allowed if the fulcrum value currently exceeds 20 centimeters and if one attempts to select a fast sweep and the fulcrum is too high, then a light is turned on to flash behind that button, as evidenced by step 268, which if no further action is taken, the program reverts to entrance point 238 and the program will continue looping and inhibit further action until a valid selection is made, at which time this information is sent into storage by step 270 and the program again will revert to entrance point 238 which if the TOMO ON and BOOST switches are on, step 234 will initiate the START TOMO subroutine 236.

Figure 11:
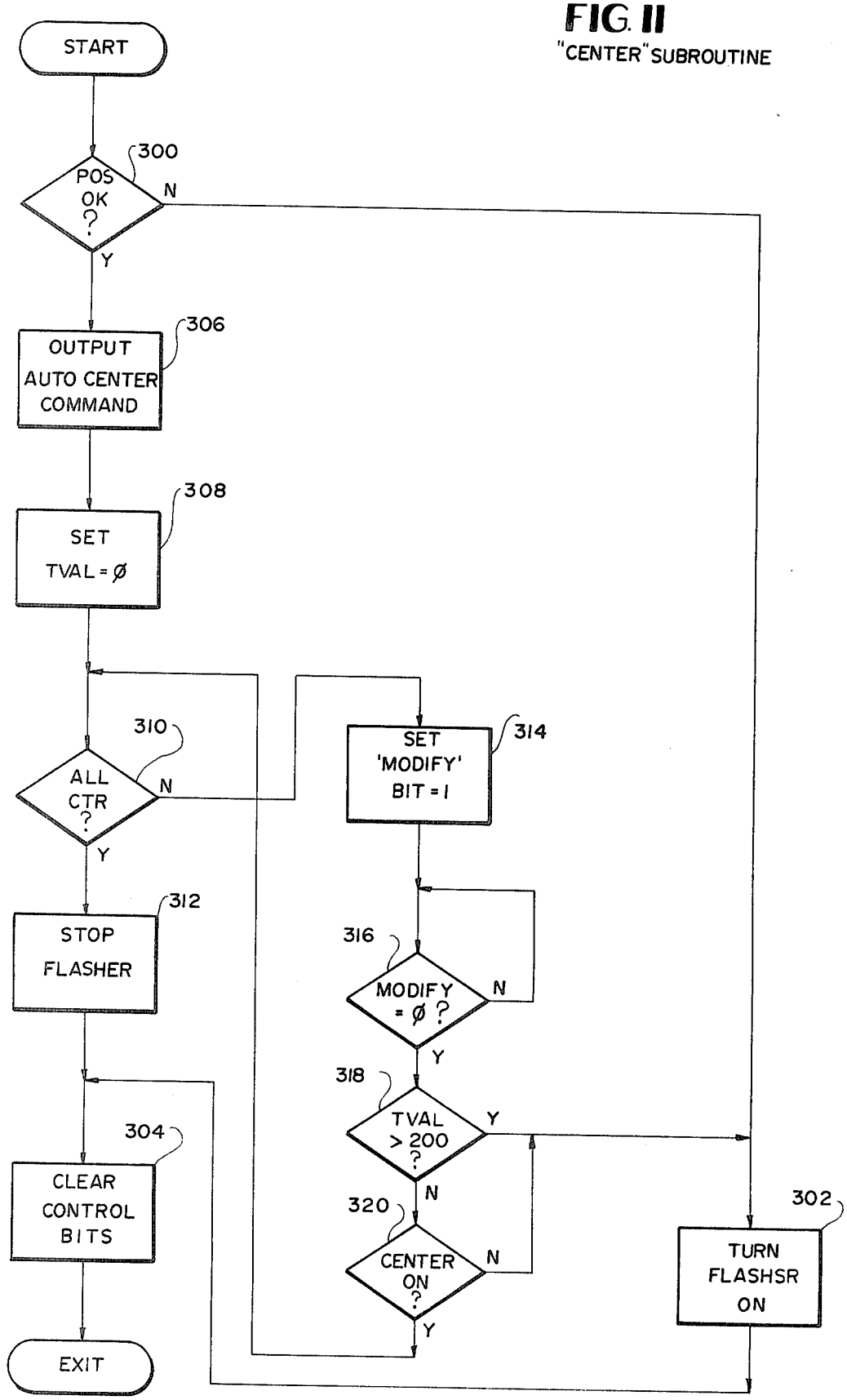
FIG. 11 is a flow chart illustrative of the CENTER subroutine shown in FIG. 10A.
Figure 12A:
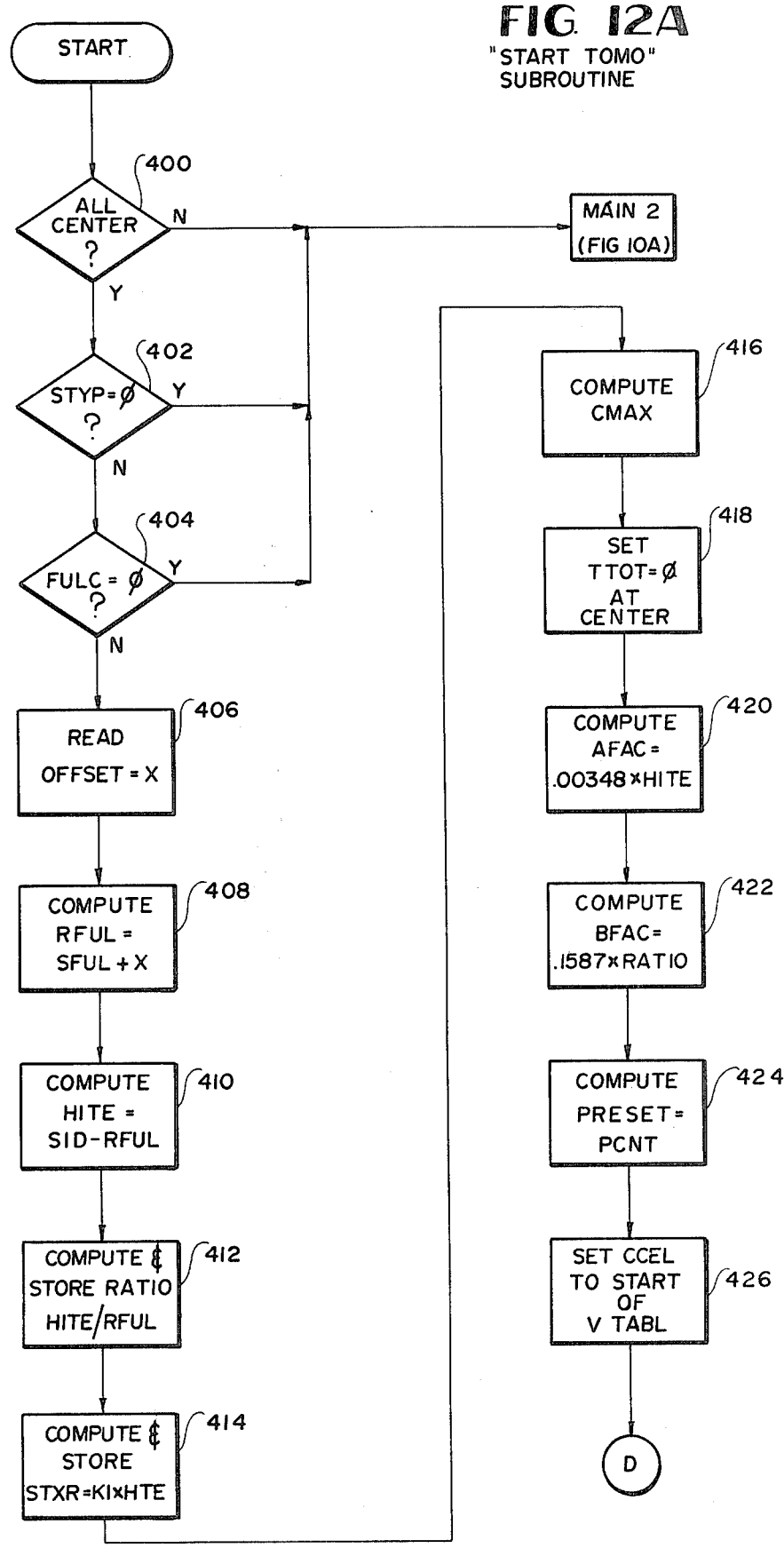
FIGS. 12A and 12B comprise a flow chart illustrative of the START TOMO subroutine shown in FIG. 10A.
Figure 12B:
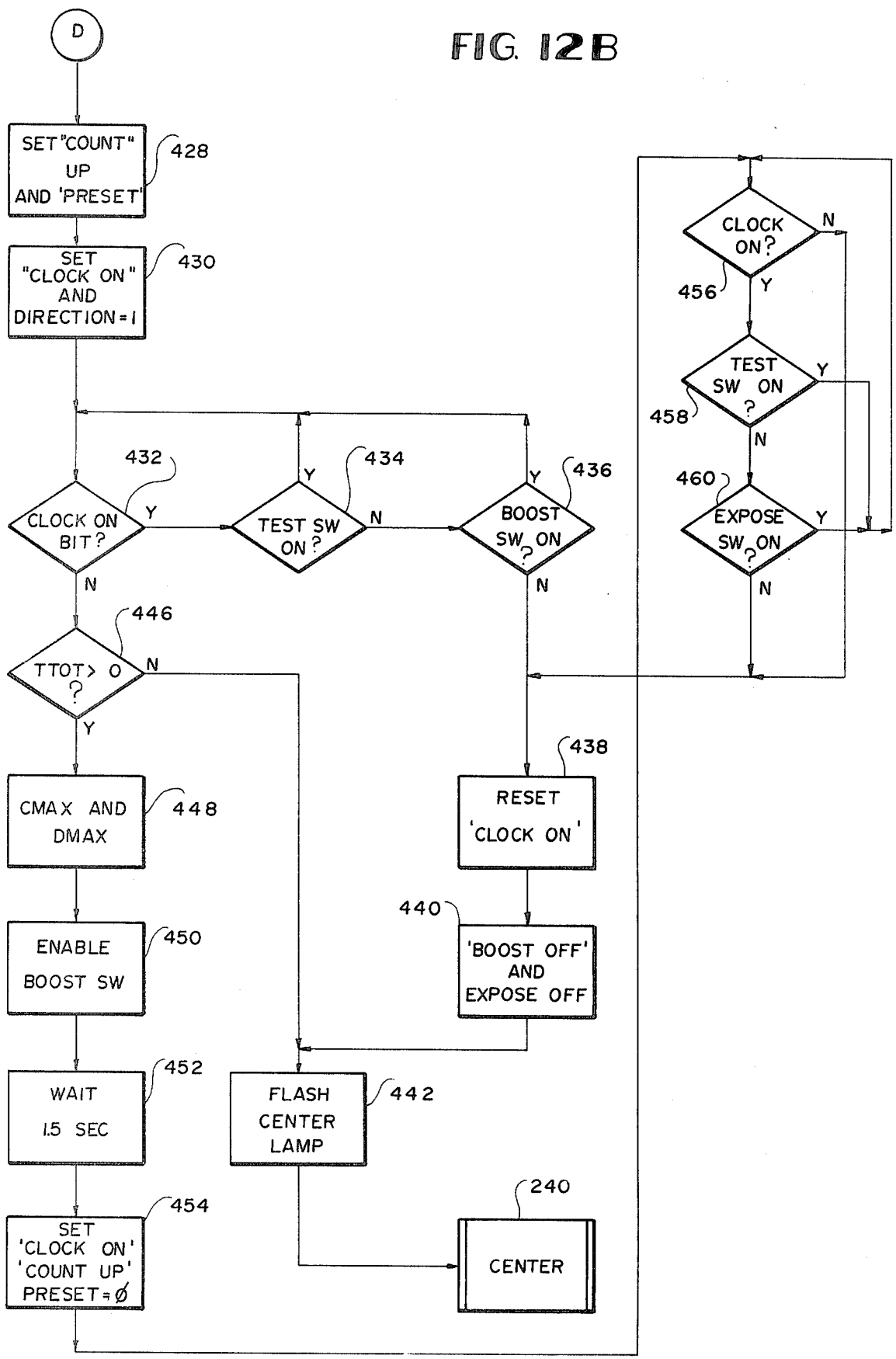

Considering now the two more pertinent subroutines of the MAIN routine, reference is now made to FIG. 11 which discloses the flow chart outlining the CENTER subroutine and which has for its primary purpose issuing the AUTO CENTER command to each of the self-centering servo loops which drive the respective stepper motors 32, 34 and 36 for the bridge 10, X-ray tube 16, and X-ray receptor 20, respectively. This routine is called by operating the CENTER switch on the operator parameter select panel 74 or under certain conditions during the START TOMO routine as will be shown subsequently. First of all, this subroutine begins by step 300 by testing for the presence of a signal indicating that all initial conditions are correct and the routine will not proceed unless the signal is present. If it does not, a flasher light turn on sequence 302 is initiated, all control bits in the computer logic are cleared as shown in step 304 and the CENTER subroutine exits. If the signal is present, the AUTO CENTER command signal is outputted in step 306, which command is shown appearing on signal lead 82 of FIG. 1, causing the bridge 10, X-ray tube 16, and receptor 20 to move to their respective "center" positions along vertical axis 27. At the same time a pulse counter value TVAL which is indicative of a total translational value of the bridge 10 is set to zero in step 308. When the three units 10, 16 and 20 are centered, a "CENTERED" signal is returned to the computer 38. Next the CENTER subroutine initiates a test 310. When the required response indicating "centered" is received, the flashing CENTER lamp will be turned off, as shown in step 312. The control bits will again be cleared as shown in step 304 and the routine will exit. If the proper response is not received for the "centered" test 310, the program will branch off into steps 314, 316 and 318. The step 314 sets a "modify bit" in the register to "1", and a test is made subsequently to see if it has been zeroed. The test 318 is to determine if the TVAL value is greater than 200, meaning that more than 10 seconds have elapsed, the limit selected for permitting centering motion. If so the auto centering operation is terminated. A test 320 again comprises a test to see whether or not the CENTER switch is on and acts as a "dead-man" switch test, causing the routine to revert back to the CENTER test set 310 if the answer is affirmative while going to step 302 if the answer is negative. In essence, the CENTER subroutine causes an output command to be issued to the auto center system and then waits for a returned signal indicating that all units are properly centered. There is no active microprocessor participation in the centering process other than the issuance of the first command and performing appropriate housekeeping.

Referring now to the START TOMO subroutine which is shown in FIGS. 12A and 12B, this is the main arithmetic code of the control program for computing certain factors needed for stepper motor control and exposure timing. Referring now to the flow chart shown in FIG. 12A, three tests 400, 402 and 404 are made to find out if for some reason the system is not "centered" or that the sweep type is set to zero, meaning no selection has been made or the fulcrum value is set to zero, the routine simply returns to the MAIN routine shown in FIG. 10A at MAIN 2 entry point 238. If all the conditions for constructing a sweep are met, meaning that everything is "centered" and a sweep type and fulcrum has been selected, the stored OFFSET value of the distance from the top of the X-ray table 20 to the film plane 30 shown in FIG. 1 is read from the unit 76 which value is set up by service personnel at installation time. This step is shown by reference numeral 406. Next a value of the real fulcrum distance RFUL is computed in step 408, which is the value of the fulcrum SFUL selected by the operator plus the OFFSET read in step 406. Next a HITE value is computed in step 410 by subtracting the real fulcrum value RFUL from the SID value, which comprises the distance between the focal point 28 and the film plane 30. Next the ratio of HITE to RFUL is computed and stored in memory as indicated by reference numeral 412.

It should be pointed out that in making a tomographic sweep, the units are driven to a preset point and then reverse direction and at some predetermined point called the start X-ray point or STXR exposure begins. This point is determined in step 414, where the value of HITE is multiplied by a factor K1, which is a factor precomputed for each of the six sweep types and contains trigonometric values required for considerations of angle tangent and mechanical ratio between bridge and receptor necessary to provide the necessary number of pulses or steps. Next a value defined as CMAX is computed at step 416, which is a value representative of the maximum speed allowable and is a means of controlling maximum velocity for a particular sweep and is based on data which may be changed at 50 millisecond intervals, i.e. during the INTERRUPT PROCESSING routine. Next a running pulse count, simply called TTOT is initialized at step 418 and set to zero. This parameter is the total pulse count which will be accumulated as the support assembly (bridge) 10 moves from the CENTER position to the PRESET position and in effect keeps track of the maximum positional change of units determined in terms of bridge motion and wherein, for example, the support assembly 10 and receptor assembly 20 will then reverse direction and move back toward the center position during the course of making the sweep and X-rays are taken. It is from the value of TTOT from which position is determined dynamically during an active sweep. All system computations are made for the support assembly drive only and the angulation and receptor assembly drives are slaved to this computation.

The TTOT value is adapted to provide the current position of the support assembly 10 in pulses or steps from "center." Also when the TTOT value equals the value of STXR as computed in step 414, X-ray exposure is enabled. Accordingly, TTOT is used to store a count as movement occurs off of "center," then as it returns to "center," the count will be decremented until the point corresponding to STXR is reached and the X-rays are turned on.

Next two extremely significant multiplication factors AFAC and BFAC are computed at steps 420 and 422. These factors are the source angulation and receptor (bucky) factors which will be used as multipliers of the frequency divider value for the support assembly 10 during any INTERRUPT PROCESSING interval, thus slaving the source stepper motor 34 and the receptor stepper motor 36 to the support drive stepper motor 32. Thus when the support stepper motor speed is determined, the values AFAC and BFAC will be used as the pulse divider factors applied to programmable dividers 86 and 88. In the subject system, the factor AFAC is a function of the HITE value previously computed, while the BFAC factor is a function of the RATIO value previously calculated in steps 410 and 412 and are based as can be shown, upon the trigonometric relationship of triangular diagram shown in FIG. 1 and the mechanical ratios of the respective drives with one assumption being made, that is the angle defined by the central axis 27 and X-ray beam 26 is assumed to be related to its tangent in a linear manner, serving to simplify computation without impairing the accuracy of the angulation control.

Following the above, based on empirical data derived on an experimental basis, a "preset" distance in pulses PCNT is computed in step 424 which comprises the maximum excursion the support assembly 10 is to take in its move away from the center position to make a tomographic sweep and is based upon a consideration that once the PRESET position has been reached, and movement initiated back towards the CENTER position, sufficient distance is built in to allow the system to overcome inertia and accelerate to the required velocity before exposure begins. The computation in step 424 considers all the necessary factors involved and assures a margin of safety for system operation. Next following computation of the PRESET distance desired for the support assembly 10, the routine sets a pointer to the start of a velocity table stored in the PROM 44 as set forth in the foregoing table. As can be seen, this table contains a series of pairs of values, one being a divider value TDIV for the bridge drive motor 32 and accordingly the value fed to the programmable pulse divider 84 and the other being the number of pulses CCNT which will be issued during the next 50 millisecond INTERRUPT PROCESSING interval during which the selected value is active. This table has been configured to provide a series of values which assures proper acceleration and deceleration of the system up to and down from whatever maximum value is required. The first cell in the velocity table is set to a zero value which is a required starting point. Next "count up" and "preset" flags are set in step 428 which simply tells the system that movement of the elements are beginning and acceleration required. The "preset" flag advises the INTERRUPT PROCESSING routine that it is not yet making a scan but moving to the PRESET position. Next step 430 occurs wherein a very important "clock on" bit is set which will activate the PRESET routine during the next 50 millisecond INTERRUPT PROCESSING interval. The "clock on" bit being set signals the INTERRUPT PROCESSING routine to activate the stepper motors and the PRESET subroutine will be in control until movement of the PRESET positioning is complete. During this time the START routine will loop in steps 432, 434 and 436.

Thus the START subroutine is simply a code which is issuing commands and while doing so, the INTERRUPT PROCESSING routine is running completely independently off on the side. The INTERRUPT PROCESSING routine, however, does not call for stepper motor action until the above mentioned "clock on" bit is set to "1." It should also be pointed out that it is the INTERRUPT PROCESSING routine which calls the PRESET subroutine. While the START subroutine is looping, during the PRESET subroutine in addition to testing for the presence of the "clock on" bit in step 432 further checks are made to make sure that either the TEST switch or the BOOST switch is still on as noted in steps 434, 436. This is simply a "dead-man" control to make sure that the operator just doesn't release the switch. Accordingly, as long as the "clock on" bit is set and one of these switches is depressed, it stays in the loop and keeps cycling so that for all appearances, the START subroutine is doing nothing and is stopped, but while it has gone into the loop, every 50 milliseconds the INTERRUPT PROCESSING routine breaks in and turns control over to the PRESET subroutine to output data to the stepper motors thereby directing the motor drive circuits 102, 104 and 106 to move the support assembly 10 and receptor assembly 20 to the "preset" position.

When the PRESET subroutine has done all that it is supposed to accomplish, it will reset the "clock on" to "0", which means that the next time that this subroutine passes test 432, the test fails and the "clock on" bit is no longer present and the START TOMO subroutine continues. It should also be pointed out that in the event the step 436 fails, the "clock on" bit is reset and "boost off" and "expose off" flags are set in step 440, the flasher for the "CENTER" lamp is activated in step 442 and the CENTER subroutine is again entered.

Returning now to step 432, if the "clock on" bit test 432 fails, a test is made to determine whether or not the value TTOT is greater than zero as evidenced by step 446. Since movement of the support assembly 10 has occurred to the "preset" position, TTOT must have a value greater than zero, otherwise a malfunction has occurred whereupon the START TOMO subroutine reverts to the CENTER subroutine 240. Under normal operation the TTOT test 446 will yield an affirmative answer, after which two values are called, namely CMAX and DMAX, where DMAX is the divider value corresponding to the maximum velocity at which the whole system must move to peak velocity during a tomographic sweep, while CMAX is the per unit pulse count corresponding to that value. Next in step 450, the BOOST switch 70 is enabled which permits the X-ray generator to be boosted in a well known manner. A waiting period of 1.5 seconds is next effected in step 452 to allow for mechanical motions to subside and then the aforementioned "clock on" bit is again set as well as the bit called "count up". The "preset" bit is also set to "0" in step 452, indicating to the INTERRUPT PROCESSING routine that the "preset" position has been reached and the sweep mode is to begin. Again, a testing loop involving steps 456, 458 and 460 is entered into, insuring that the "clock bit" is on, that the TEST switch is off, and the EXPOSE switch is on. This loop will continually recycle until such time as the "clock on" bit is turned off as sensed in step 438, whereupon the system will revert to the CENTER subroutine 240 at the end of a tomographic sweep.

In order to maintain a sense of clarity of overall system operation, mention at this point requires considering the INTERRUPT PROCESSING routine and its PRESET subroutine which have been referred to above. As already noted, INTERRUPT PROCESSING is called automatically at 50 millisecond intervals once enabled by step 202 shown in FIG. 10A of the MAIN routine. This routine will execute without regard to what may be taking place elsewhere in the system once enabled. Operation of this routine requires only a few milliseconds each interval so that its effect on total system operation is essentially invisible. Its purpose, however, as already mentioned is to output all data, execute the subroutines which control system motion, and to service miscellaneous timing functions for its subroutines.

Referring now to FIG. 13 which comprises a flow chart for INTERRUPT PROCESSING, a test is made at step 500 to determine whether or not the CLOCK ON/OFF switch on the panel 74 (FIG. 1) has been activated. If it has been activated, the auxiliary timer will be tested at 502 to determine its state. If the time is not set at zero, time is decremented in step 504 until time is zero with a testing step being made at 506, at which time a buzzer is sounded, signifying at step 508 that a required elapsed time has taken place. If the timer switch is off and the timer is set to zero and the program proceeds to step 510 where a test is made to determine whether or not the "clock on" flag is set. If there is no "clock on" flag, no system motion is required and operation proceeds to a DISPLAY subroutine 512, where all output data will be displayed and a utility value TVAL will be tested and modified if required in steps 514, 516 and 518. TVAL is used by other subroutines, timing certain functions, but is not significantly important to dwell upon or offer further explanation.

Going back to step 510, however, if the "clock on" flag is set, it tests step 520, which is made to determine whether or not the system should be moved to the "preset" position which as noted before, occurred during the START TOMO subroutine to indicate that motion to the "preset" position is required. If "preset" is complete, control is transferred to the NEXT subroutine 524 which will be considered subsequently.

Figure 14:
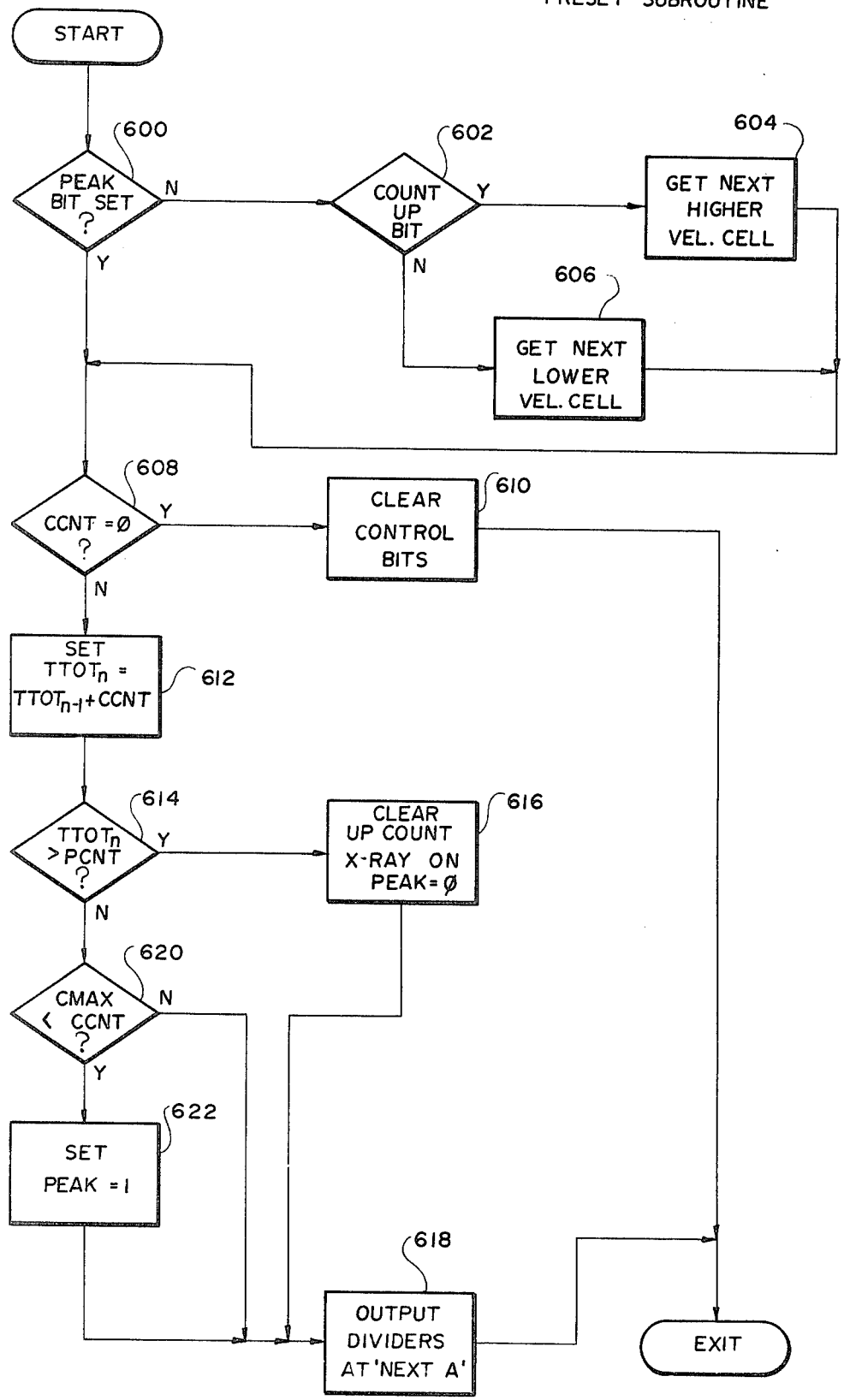
FIG. 14 is a flow chart illustrative of the PRESET subroutine shown in FIG. 13.

Reference will now be made to the flow chart shown in FIG. 14, which outlines the PRESET subroutine. This subroutine, as already noted, can only be executed if the INTERRUPT PROCESSING routine finds the "clock on" bit set. Now a test is made in step 600 for the condition of a "peak" bit. The purpose of the "peak" bit is to let the subroutine know that maximum velocity of the support assembly or bridge stepper motor 32 has been reached. It is initially zero as required in the velocity table set forth above. If the subroutine is entered and found that the "peak" bit is not set, then a "count up" bit is checked in step 602 which is initially set back in the START subroutine. If the "count up" bit is set, then the pointer is directed in step 604 to go to the next higher velocity cell in the velocity table, while if the count bit has not been set i.e. is "0", the pointer goes to the next lower cell in step 606. As noted, these cells contain current divider values TDIV and pulse counts CCND, the latter being a "current count". It is the divider value, TDIV, which controls the speed of the support assembly (bridge) 10, by being inputted to programmable pulse divider 84 (FIG. 1) while the other parameter, CCNT, is the number of pulses which are expected to be generated during the next 50 millisecond INTERRUPT PROCESSING interval. In any event, the current count CCNT is tested at step 608. If it is zero which it can only be because the pointer had moved back to the start of the table where zero values are stored and this is interpeted to mean that the system has decelerated to a stop. Accordingly, if CCNT equals zero, all control bits including the "clock on" bit are cleared and the subroutine exits. If the current count (CCNT) has a non-zero value, it is added to the previous value of TTOT in step 612 where a running total of motion off center is saved. Next the new value of TTOT is checked against the previously determined maximum preset distance or PCNT as computed in step 424 (FIG. 12A). If the new TTOT value is greater than PCNT, it indicates that the end of the required "preset" travel has been reached. Accordingly at step 616 the "up count" value is cleared, as a precautionary measure the "X-RAY ON" bit is cleared, and the "PEAK" bit is set to "0" to permit deceleration of the stepper motor 32. This will cause subsequent executions of this subroutine to step the system down to zero speed. Following this, the step 618 occurs wherein the other divider values i.e. the pulse divider 86 for the source angulation and the pulse divider 88 for the receptor, are outputted during the subsequent NEXT subroutine. Referring back to step 614, if the new TTOT value is less than PCNT, operation continues to step 620, where the pulse count corresponding to the maximum allowed velocity or CMAX is compared against the current count CCNT. If CMAX is greater than CCNT, no special action is taken, but if the current value is greater indicating that maximum velocity is reached, the PEAK bit is set in step 622 and further acceleration is prohibited, at which time the routine exits through step 618 as before.

Figure 15:
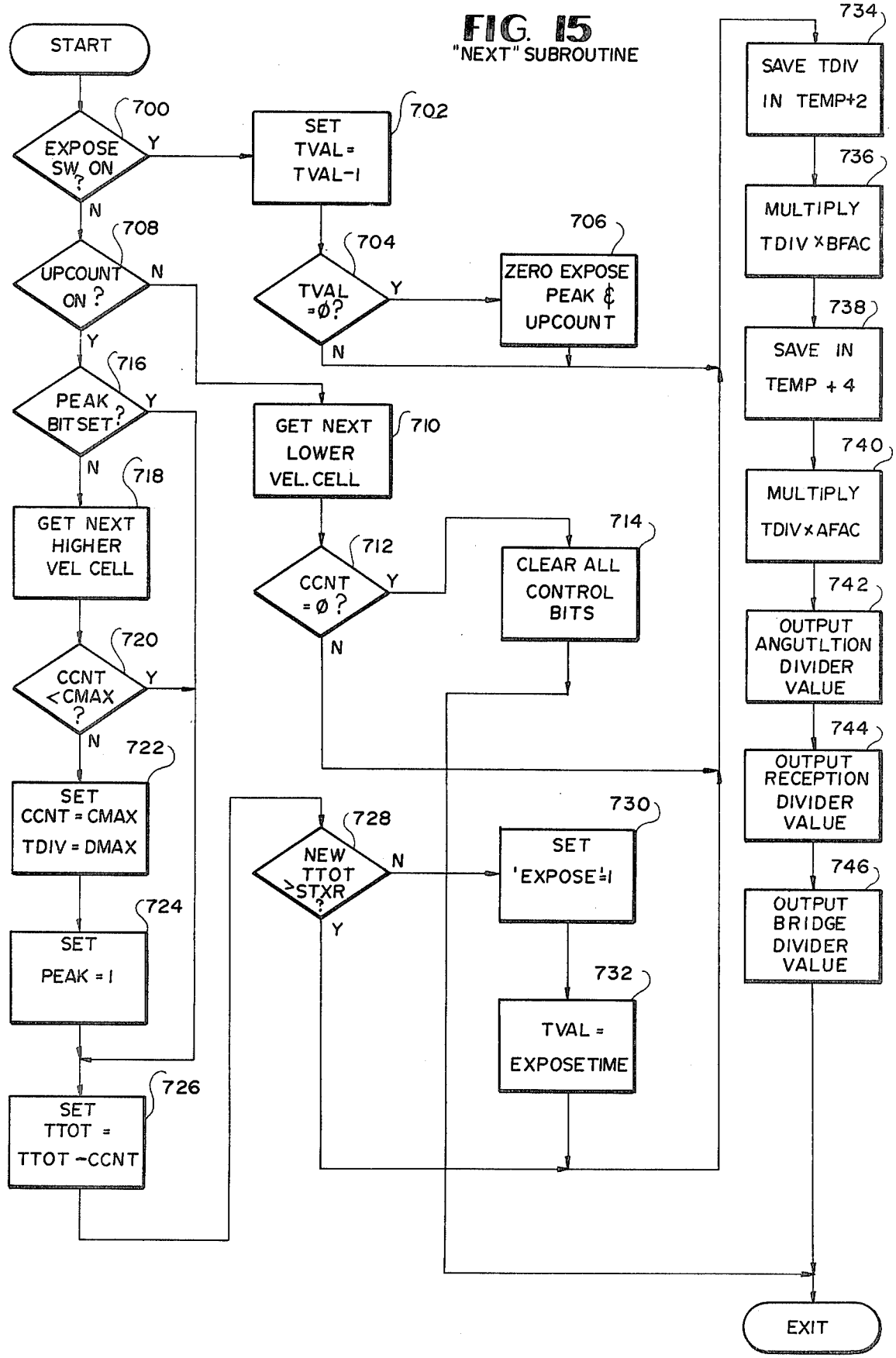
FIG. 15 is a flow chart illustrative of the NEXT subroutine shown in FIG. 13.

Referring now to the NEXT subroutine, the flow chart of which is shown in FIG. 15, it is in this subroutine that the sweep motion control resides. This code is executed only when the INTERRUPT PROCESSING routine finds the "clock bit" set and the "preset" bit is not set, meaning that PRESET subroutine has been completed. Operation begins at step 700 by testing the EXPOSE switch 72, (FIG. 1). If it is ON, then X-ray exposures have already been enabled, and it is required only that the controlling value TVAL be decremented in step 702. TVAL has previously been initialized to a value corresponding to the pulse count value required over the X-ray exposure time and that is being successively decremented on a pulse by pulse basis and a test is continually made at step 704 to determine whether or not the TVAL is equal to zero meaning that the X-ray is to be turned off. As TVAL is decremented to zero, it is tested at step 704 and at step 706 where TVAL=0, the EXPOSE, PEAK and UPCOUNT bits are zeroed to enable system deceleration at step 706. If the EXPOSE switch is not on as tested in step 700, a test is made at step 708 to determine whether or not acceleration or deceleration of the system is in progress. If the "upcount" bit is "0", the program will fetch the next lower velocity cell from the table in step 710. If the fetch retrieves the zero count cell which is tested in step 712 whereby the current count (CCNT) is zero, the sweep is over and the control moves to step 714 where all control bits are cleared and the routine exits, stopping the system.

If the "upcount" bit is "1", as tested in step 708, a test is made in step 716 of the "peak" bit which if it is set i.e. at "1" indicating that the system motion is at the required maximum velocity, no new data will be retrieved or fetched from the velocity table, otherwise the next higher velocity cell will be fetched in step 718. The current pulse count CCNT found in the new cell is tested in step 720 against the computed CMAX value computed in step 448 shown in FIG. 12B of the START subroutine. If CCNT exceeds CMAX, then the new current count and the divider value TDIV in the next higher cell will replace the previous values in step 722. The "peak" bit will be set to "1" in step 724 to prevent further acceleration and operation moves to step 726 where the previous TTOT value will now be reduced by the value of the new CCNT in step 726, which new TTOT value is next tested against the computed "start X-ray" point (STXR) in step 728. If the point is reached, meaning that the bridge 10 has moved to within the exposure range desired, the EXPOSE bit will be set in step 730 and the value of TVAL will be set to a fixed value in step 731, corresponding to the number of 50 millisecond interrupt processing intervals in the required exposure time. This is the value which will be decremented at step 702 to time out the exposure.

This approach to exposure timing assures total exposure durations which are as accurate as the number of 50 millisecond timing INTERRUPT PROCESSING intervals used. Whether or not the "expose" bit is set, the NEXT subroutine continues to step 734 where the current frequency divider value TDIV for the support stepper motor 32 to be outputted from the programmable frequency divider 84 (FIG. 1) for the next 50 millisecond interrupt period is saved temporarily. This TDIV value is next multiplied by the term BFAC in step 736 to derive the corresponding frequency divider value to be outputted from the programmable frequency divider 88 (FIG. 1) for the receptor stepper motor 36 and is temporarily saved in memory at step 738. The same procedure is again followed in step 740 whereby the TDIV value is multiplied by the term AFAC to determine the source's angulation frequency divider value to be outputted from the programmable frequency divider 86. With the three frequency divider value computations for the programmable frequency dividers 84, 86 and 88 thus completed, all three values are outputted substantially simultaneously to the respective motor drive circuits 102, 104 and 106 via the respective drive logic circuits 92, 94 and 96 in steps 742, 744 and 746. The divider data is outputted in a group to minimize the total time elapsing between successive outputs so that the possibility of two drives that were running at unsynchronized frequencies can be reduced to insignificance. Following this, the NEXT subroutine exits and returns control to the INTERRUPT PROCESSING routine.

It should be noted that the NEXT subroutine is shared by the PRESET subroutine during steps 734–746. Also, it should be noted that once an X-ray exposure has been started, no changes are made in the output dividers and operation is continuous until the exposure period is timed out, at which time control is returned to the code which manages the deceleration of the stepper motors.

Figure 17:
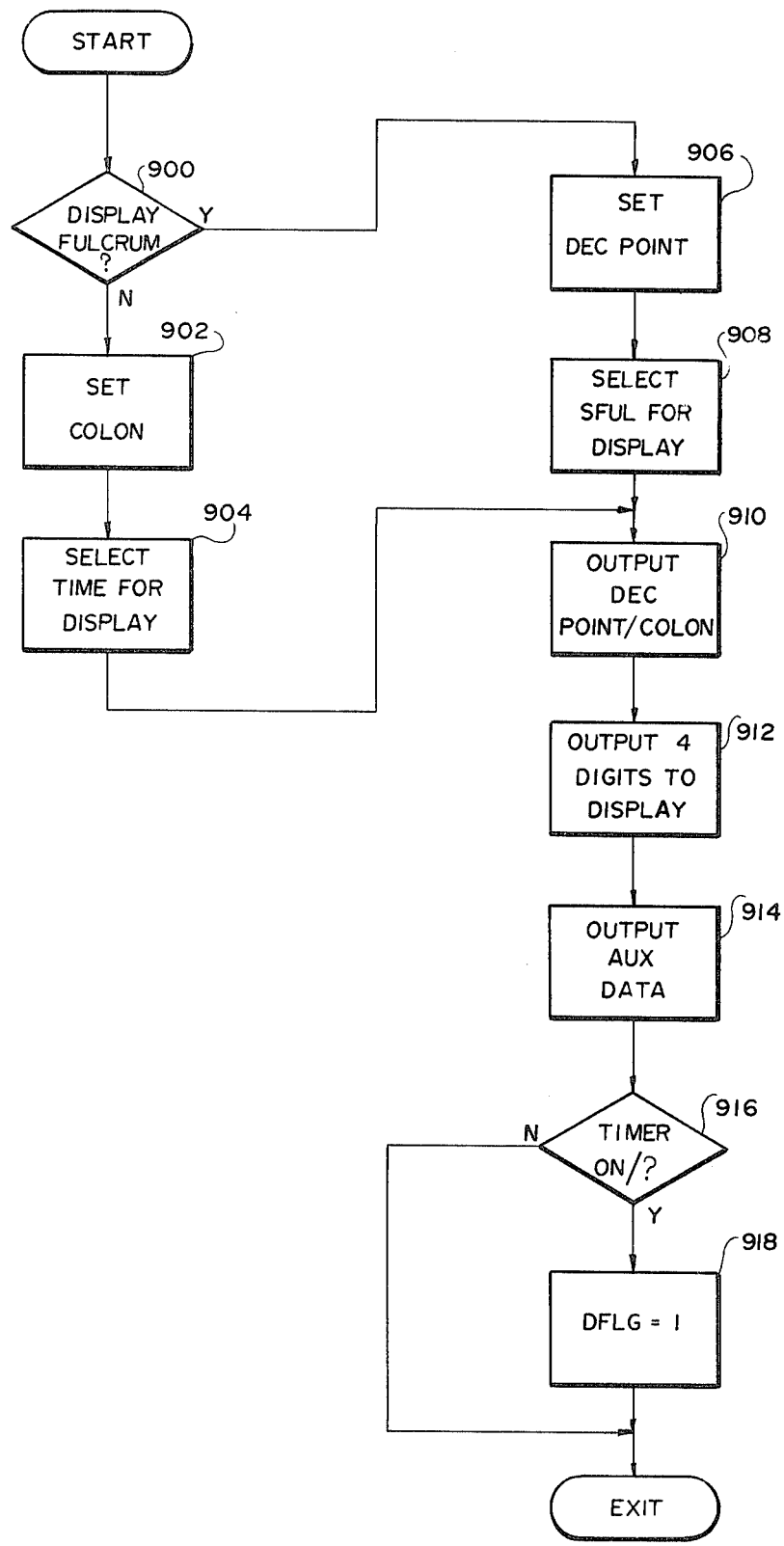
FIG. 17 is a flow chart illustrative of the DISPLAY subroutine shown in FIG. 14.

As referred to earlier, the MAIN routine also includes a CHANGE subroutine whose flow chart is shown in FIG. 16, and the INTERRUPT PROCESSING routine also includes a DISPLAY subroutine, whose flow chart is shown in FIG. 17. These subroutines are interrelated in that the CHANGE subroutine determines whether the auxiliary timer value or the fulcrum value selected is to be displayed by the operator, whereas the DISPLAY subroutine actually effects the display of such values on the display 100, as shown in FIG. 1. Considering first FIG. 16, this subroutine is called by operating either the UP or DOWN switches on the control panel 74 shown in FIG. 1. The CHANGE subroutine begins by testing to see whether or not the auxiliary timer is running at step 800. If it is not running, then it is assumed that it is time which is to be displayed and therefore time which is to be incremented or decremented. If the test 800 indicates that the auxiliary timer is running, then it is assumed that fulcrum value is to be displayed and accordingly the subroutine includes two separate branches from either time or fulcrum, depending upon the results of the test 800. If time is to be displayed, the subroutine moves to a test 802 to see whether time is to be increased or decreased, which is indicated by testing the steps 246 and 250 of the MAIN routine shown in FIGS. 10A and 10B. If the current value in minutes is equal to 60, the routine jumps to step 806, whereupon the second's value is set to zero and the DISPLAY TIME command is given at step 808. If a time decrease is indicated by step 802, a test 810 is made to determine whether or not the minutes value is equal to zero. If the answer is affirmative, the routine again branches to steps 806 and 808. Accordingly, if time increment can be made resulting from test 804 an order of one minute increments at step 812 is made or a decrement in one minute intervals is made in step 814, a delay of 0.5 seconds in step 816 which permits two changes per second to be made, and the routine proceeds to the exit point through steps 806 and 808.

Considering the parallel code for fulcrum values, a test 818 is again made to determine if the B value is "1" or "0". If the fulcrum value is zero according to the test step 820, no further decrement can be made and the routine skips to the display fulcrum and commands step 822 and the subroutine exits. If the fulcrum value is not zero, the step 824 effects a decrement of fulcrum value by one count, a delay of 0.3 seconds is effected, step 826, and the display step 822 is entered into. If an increment has been ordered for step 818, a check is made at step 828 to see if the fulcrum value is equal to 55 which, for example, is the fifty-fifth position corresponding to $27\frac{1}{2}$ centimeters counted in half centimeter steps. If the fulcrum is at the maximum position, the subroutine proceeds to step 822 and exits. If the fulcrum value is not at the maximum value of 55 steps, a test is made to see if the fulcrum value is at the 40th position, which corresponds to 20 centimeters. At that point, a test is made at step 832 to see if a fast sweep has been selected, because the fulcrum cannot be incremented using fast sweeps in the present system for fulcrum setting equal to or greater than 20 centimeters. If a fast sweep has not been selected, the fulcrum is incremented by one count in step 834 and delayed 0.3 seconds again in step 826 permitting the fulcrum decrements at the rate of 3 per second to be made. Again, the display fulcrum command 822 is made and the routine exits.

As noted before, the DISPLAY subroutine as shown by the flow chart of FIG. 17 is called during the INTERRUPT PROCESSING routine shown in FIG. 13. It first determines which display is required in step 900 by testing for the presence of a "display funcrum" bit. If time is to be displayed, test step 900 proceeds to step 902 whereupon the (:) is set for the designation between minutes and seconds. Next step 904 selects the time for display whereupon it proceeds to output the time for display. If the fulcrum is to be displayed, step 906 is initiated, whereupon the decimal point is set for the fulcrum display with the value of the operator selected fulcrum SFUL selected for display is retrieved, step 908. The two branches converge at step 910, whereupon either the decimal point (.) or the colon (:) is outputted at step 910, along with the four digits of the value to be displayed at step 912. Following this, all the auxiliary control data such as motor direction, boost, expose, enable and flasher control will be outputted in step 914.

As a final check, the subroutine will sample the "timer on" bit at step 916, which if it is on, will assure that the display fulcrum flag is set to "1" in step 918. The last operation 918 is to assure that the operation of the display time switch has only temporary effect.

It will be appreciated from the foregoing that the operational code which controls motor motion is operative only intermittently, i.e. when called by the INTERRUPT PROCESSING routine. Following the CENTER subroutine the program most visible during this time is the START subroutine of the MAIN routine which is sampling the switch status of the TEST and BOOST or EXPOSE switches while waiting for the "clock-on" bit to be cleared. Thus when the PRESET or NEXT subroutine is called during the INTERRUPT PROCESSING routine, it operates only to examine the then current status of the system, decide what is to take place during the next 50 milliseconds, and thereafter output any new divider values to the programmable frequency dividers which may be required and then exit back to the INTERRUPT PROCESSING routine, which in turn will return control to the START subroutine.

There are a number of instances wherein operations appear to be redundant; however, these appear because the code may be entered from several points, some of which may not contain the required bookkeeping. This redundancy is merely precautionary. There is also liberal use of "dead man" fail safe controls, the intent being that the system elements are to be allowed to move only if the operator is maintaining a closed contact of an appropriate switch control.

As described, all computations are made at the start of a 50 millisecond interval, following self-centering and motion of the support assembly or bridge 10, the X-ray tube 16 and the receptor assembly 20 only travel in accordance with the pulses applied thereto in 50 millisecond intervals. This time frame, however, gives the appearance of continuous motion.

While there has been shown and described what is at present considered to be the preferred embodiment of the subject invention, modifications thereto will readily occur to those skilled in the art. It is not desired, therefore, that the invention be limited to the specific method steps and arrangements of components shown and described, but it is to be understood that all equivalents, alterations and modifications coming within the spirit and scope of the present invention as defined in the appended claims are herein meant to be included.

We claim as our invention:

1. A method for non-mechanically linking the motions of an X-ray source with an X-ray receptor during a tomographic procedure to produce a tomograph of a section of an object under examination comprising the steps of:
    effecting motion of said source and receptor to respective reference positions;
    thereafter during a tomographic procedural mode generating from at least one fixed frequency signal source first and second pulse trains, adapted to drive respective stepper motors, for effecting motion of said source and receptor, said pulse trains having a predetermined mathematical relationship dependent upon the desired fulcrum height of the tomographic section to be produced; and
    applying said first and second pulse trains to the respective stepper motors for a predetermined number of pulse counts to effect motion with respect to said respective reference positions and effecting a tomographic sweep thereby.

2. The method as defined by claim 1 and additionally during said tomographic procedural mode generating from said signal source a third pulse train also having a predetermined mathematical relationship with said first and second pulse trains;
    applying said third pulse train to another stepper motor coupled to said source for a predetermined pulse count to cause angular rotation of said source for pointing said source to substantially the same location on said receptor during said tomographic procedure.

3. The method as defined by claim 2 wherein said step of generating said pulse trains comprises generating said three pulse trains under the control of a stored routine of a digital computer.

4. The method as defined by claim 3 wherein said step of generating and applying said pulse trains to said stepper motors comprises accessing a memory in said computer having a table of stored frequency divider values;
    outputting a predetermined frequency divider value to a programmable frequency divider coupled to said fixed frequency signal source and outputting a divided pulse train derived from said signal source to control one of said stepper motors;
    performing a first mathematical operation in said computer on said pulse frequency divider value and outputting a new frequency divider value to another programmable frequency divider and outputting a pulse count derived from said fixed frequency signal source for controlling another of said stepper motors;
    performing a second mathematical operation in said computer on said predetermined frequency divider value and outputting another new frequency divider value to still another programmable frequency divider and outputting another new pulse count derived from said signal source for controlling the remaining stepper motor.

5. The method as defined by claim 4 and additionally including the step of outputting said predetermined frequency divider values at periodic time intervals during said routine.

6. The method as defined by claim 4 wherein said predetermined frequency divider value is coupled to a programmable frequency divider for controlling movement of a support upon which said source is mounted and wherein said first recited stepper motor is adapted to effect movement of said support.

7. The method as defined by claim 4 wherein said step of performing said first and second mathematical operation comprises multiplying said frequency divider value by respective calculated factors which are based upon the distance separation (S.I.D.) between the source and receptor, the height separation (SFUL) between the fulcrum level and the surface of the support on which said object is placed and distance (OFFSET) between the surface of said support and the surface of said receptor.

8. The method as defined by claim 1 and additionally including a step of initiating X-ray exposure after a predetermined time subsequent to the beginning of said tomographic procedure and terminating exposure at a predetermined time prior to the end of said tomographic procedure by generating and applying control signals to the X-ray exposure control circuitry, said first and second pulse trains being applied at variable frequencies dependent upon the desired exposure time to effect acceleration of said source and receptor to and from a predetermined constant velocity during said exposure time.

9. The method as defined by claim 1 wherein said step of applying said first and second pulse trains effect a linear tomographic sweep during said tomographic procedure.

10. The method as defined by claim 1 wherein said step of effecting motion of said source and receptor to respective reference positions comprises first moving said source and receptor to a first position wherein said source and receptor are in mutual alignment along a common axis and thereafter moving said source and receptor in mutually opposite directions to a second position which is a predetermined distance away from said common axis dependent upon the operational parameters inputted to the system by an operator.

11. The method as defined by claim 10 wherein said step of effecting motion of said source and receptor to said reference position is under the control of a stored program digital computer.

12. The method as defined by claim 1 wherein said step of applying said first and second pulse trains effect motion of said source and receptor in radial directions toward a system center of rotation, and
additionally generating a third pulse train for causing a rotational motion of said source and receptor about the system center of rotation to effect circular, spiral and other generalized types of tomographic procedures.

13. A drive system for non-mechanically linking the motions of an X-ray source and an X-ray receptor through a predetermined fulcrum point during a tomographic procedure comprising, in combination:
first and second drive motors respectively coupled to and being operable to simultaneously move said X-ray source and said X-ray receptor in response to respective drive signals applied thereto;
first circuit means responsive to a first digital control signal to generate and apply drive signals to said drive motor coupled to said X-ray source,
second circuit means responsive to said second digital control signal to generate and apply drive signals to said drive motor coupled to said X-ray receptor; and
digital control means comprising a stored program digital computer responsive to at least one selected input parameter for a predetermined operating sequence and being operable thereafter to generate said first and second digital control signals having a predetermined mathematical interrelationship based on a selected fulcrum height and the type of tomographic procedure desired, said stored program digital computer being operable in accordance with stored digital instructions and having a memory programmed with successive velocity data values of drive motor operation and additionally including means for periodically accessing said memory to apply said data values in a predetermined sequence to a selected one of said first and second circuit means and additionally including means for scaling said values by computer calculated factors based on said fulcrum point and tomographic procedure desired and to apply said factors selectively to the other of said first and second circuit means.

14. A drive system for non-mechanically linking the motions of an X-ray source and an X-ray receptor through a predetermined fulcrum point during a tomographic procedure comprising, in combination:
a first stepper motor coupled to and operable to move said X-ray source, a second stepper motor respectively coupled to and operable to move said X-ray receptor, and a third stepper motor respectively coupled to and being operable to angularly rotate said X-ray source, said first, second and third stepper motors being operable in response to respective pulse signals applied thereto;
a reference frequency signal source;
first circuit means coupled to said reference frequency signal source and being responsive to a first digital control signal to generate and apply pulse signals to said first stepper motor coupled to said X-ray source;
second circuit means coupled to said reference frequency signal source and being responsive to a second digital control signal to generate and apply pulse signals to said second stepper motor coupled to said X-ray receptor;
third circuit means coupled to said reference frequency signal source and responsive to a third digital control signal to generate and apply pulse signals to said third stepper motor coupled to said X-ray source for providing angular rotation thereof; and
digital control means responsive to at least one selected input parameter for a predetermined operating sequence and being operable thereafter to generate said first, second and third control signals having a predetermined mathematical interrelationship based on a fulcrum height and the type of tomographic procedure desired, said digital control means comprising a stored program digital computer operable in accordance with stored digital instructions and having a memory programmed with successive data values corresponding to the frequency of pulse signals to be applied to at least one of said stepper motors, said pulse signals being derived from said reference frequency signal source, including means for periodically accessing said memory to apply said values to a selected one of said first, second and third circuit means and additionally including means for scaling said values by factors based on said fulcrum point and the tomographic procedure desired and to apply said values thus scaled selectively to the other of said first, second and third circuit means to affect the frequency of the pulse signals applied to the respective stepper motors controlled thereby.

15. The system as defined by claim 14 wherein said reference frequency signal source comprises a master oscillator.

16. A drive system for non-mechanically linking the motions of an X-ray source and an X-ray receptor through a predetermined fulcrum point during a tomographic procedure comprising in combination:
first and second drive motors respectively coupled to and being operable to simultaneously move said X-ray source and said X-ray receptor in response to respective first and second pulse trains applied thereto;
digital control means responsive to at least one selected input parameter for a predetermined operating sequence and being operable thereafter to generate first and second digital control signals having a predetermined mathematical interrelationship based on a selected fulcrum height and the type of tomographic procedure desired;

a fixed frequency signal source acting as a frequency reference;

first circuit means coupled to said fixed frequency signal source and being operable in response to said first digital control signal to generate and apply said first pulse train to the stepper motor coupled to said X-ray source;

second circuit means coupled to said fixed frequency signal source and being operable in response to said second digital control signal to generate and apply said second pulse train to the drive motor coupled to said X-ray receptor;

said first and second circuit means respectively including first and second programmable frequency divider circuits coupled to said fixed frequency signal source, said first digital control signal being adapted to control the division of the frequency output of said first programmable frequency divider circuit and thereby generate said first pulse train and said second control signal being operable to control the frequency division of the frequency output of said second programmable frequency divider circuit and thereby generate said second pulse train.

17. The system as defined by claim 16 wherein said digital control means comprises a stored program digital computer.

18. The system as defined by claim 16 wherein said digital control means comprises a computer operable in accordance with a stored operational code to assume overall control of said system, said computer including a memory having stored numbers in binary form corresponding to a plurality of frequency divider factors and including means for accessing said memory to periodically output predetermined frequency divider factors to said programmable frequency dividers for controlling acceleration and velocity of said drive motors.

19. The system as defined by claim 18 wherein said computer is operable in a scanning mode to examine internal control means for directing control to programs in different sections of the stored digital instructions in accordance with inputted control parameters, said computer additionally including circuit means for periodically interrupting the scanning mode to effect outputting of changes in operating parameters to the system.

20. The system as defined by claim 19 and additionally including digital means coupled to said computer for inputting thereto an OFFSET signal corresponding to the distance between the top of a patient support and a film plane of said receptor for permitting compensation for different patient supports and film plane distance without altering said stored digital instructions.

21. The system as defined by claim 16 and additionally including a third drive motor coupled to and being operable to angularly rotate said X-ray source in response to a third pulse train applied thereto, wherein said digital control means is additionally operable to generate a third digital control signal having a predetermined mathematical interrelationship with said first and second control signals; and third circuit means coupled to said fixed frequency signal source and being operable in response to said third digital control signal to generate and apply said third pulse train to said third drive motor, said first, second and third pulse trains being mathematically related by the control of said digital control means to cause said source and said X-ray receptor to remain substantially colinear through said fulcrum point during said tomographic procedure, said third circuit means respectively including a third programmable frequency divider circuit coupled to said fixed frequency signal source, said third digital control signal being adapted to control the division of the frequency output of said third programmable frequency divider circuit and thereby generate said third pulse train.

22. The system as defined by claim 21 wherein said digital control means comprises a stored program digital computer having a memory programmed with binary information corresponding to selectable motor velocity controlling values representing a predetermined distance that said source is to be moved within a predetermined unit of time and wherein said values are applied to a selected one of said first, second and third circuit means, and wherein said computer is adapted to calculate certain submultiples of said values which are applied to the other of said first, second and third circuit means.

23. The system as defined by claim 21 wherein said drive motors are comprised of stepper motors.

24. The system as defined by claim 21 wherein said fixed frequency signal source comprises a master oscillator circuit and additionally including circuit means coupling said master oscillator circuit to said first, second and third circuit means for providing a common pulse source for the generation of said first, second and third pulse trains.

25. The system as defined by claim 21 and additionally including a respective self-centering closed loop servo sub-system respectively coupled to each drive motor and being operable in response to a command signal from said digital control means to effect movement of said X-ray source and receptor to a co-linear position along a common axis.

26. The system as defined by claim 25 wherein each self-centering sub-system includes a voltage controlled oscillator adapted to provide drive signals to a respective drive motor and additionally including a respective drive logic circuit coupled to said drive motor and being operable to couple drive signals from a voltage controlled oscillator to said drive motor during a self-centering mode and from the respective one of said first, second and third circuit means during the tomographic procedural mode.

* * * * *